(12) United States Patent
Youn et al.

(10) Patent No.: US 10,370,364 B1
(45) Date of Patent: Aug. 6, 2019

(54) SUBSTITUTED CHROMENES FOR TREATMENT OF FIBROSIS OR NON-ALCOHOLIC STEATOHEPATITIS

(71) Applicant: OSTEONEUROGEN INC., Seoul (KR)

(72) Inventors: Byung Soo Youn, Seoul (KR); Jun Hwan Kim, Incheon (KR); Han Soo Kim, Seoul (KR); Ho Sup Yoon, Nanyang (SG); Ik Hwan Kim, Seoul (KR)

(73) Assignee: OSTEONEUROGEN INC., Seoul (KR)

( * ) Notice: Subject to any disclaimer, the term of this patent is extended or adjusted under 35 U.S.C. 154(b) by 0 days.

(21) Appl. No.: 16/036,949

(22) Filed: Jul. 17, 2018

(30) Foreign Application Priority Data

Feb. 27, 2018 (KR) .................. 10-2018-0023415

(51) Int. Cl.
*A61K 31/352* (2006.01)
*C07D 311/22* (2006.01)
*C07D 405/12* (2006.01)
*A23L 33/10* (2016.01)

(52) U.S. Cl.
CPC .......... *C07D 405/12* (2013.01); *A23L 33/10* (2016.08); *A23V 2002/00* (2013.01)

(58) Field of Classification Search
CPC ...................... A61K 31/352; C07D 311/22
USPC .......................................... 514/456; 549/399
See application file for complete search history.

(56) References Cited

FOREIGN PATENT DOCUMENTS

| KR | 10-1127158 B1 | 3/2012 |
| KR | 10-1135574 B1 | 4/2012 |
| KR | 10-1248295 B1 | 3/2013 |
| KR | 10-1627602 B1 | 6/2016 |

OTHER PUBLICATIONS

Yifan Wang et al., "The Role of Snail in EMT and Tumorigenesis", Curr Cancer Drug Targets. Nov. 2013 ; 13(9): 963-972.
Ching-Yi Liu et al., Vimentin contributes to epithelial-mesenchymal transition cancer cell mechanics by mediating cytoskeletal organization and focal adhesion maturation, Oncotarget, vol. 6, No. 18, Jun. 30, 2015, pp. 15966-15983.
Luis Calzadilla Bertot et al., "The Natural Course of Non-Alcoholic Fatty Liver Disease", International Journal of Molecular Sciences, May 20, 2016;17(5).

*Primary Examiner* — Douglas M Willis
(74) *Attorney, Agent, or Firm* — Revolution IP

(57) ABSTRACT

A compound represented by the following Formula 1 or a pharmaceutically acceptable salt thereof:

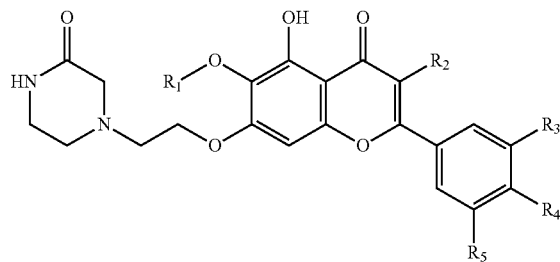

Formula 1 wherein $R_1$ is a substituted or unsubstituted $C_{1-5}$ linear or branched alkyl, a $C_{5-6}$ cycloalkyl, a $C_{5-6}$ cycloalkyl containing at least one heteroatom selected from among O and N, a substituted or unsubstituted $C_{6-12}$ aryl, or a $C_{5-6}$ heteroaryl containing at least one heteroatom selected from among O and N; $R_2$ is hydrogen, ethyl, acetyl, acetoxy, carboxy, benzoyloxy or 3,4,5-trihydroxybenzoyloxy; and $R_3$ to $R_5$ are each independently hydrogen, hydroxyl, methyl, methoxy, acetoxy, carboxy or benzoyloxy.

12 Claims, 43 Drawing Sheets

Formula 1

| Compound | Structure | Before treatment with TGF-b | 24hr after treatment with TGF-b & compound | 48hr after treatment with TGF-b & compound |
|---|---|---|---|---|
| Comparative compound1 | 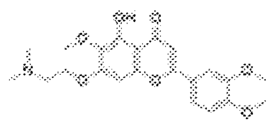 | | | |
| Comparative compound2 | 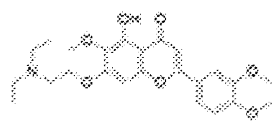 | | | |
| Comparative compound3 | 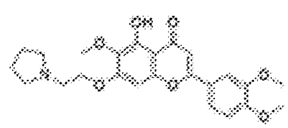 | | | |

FIG. 24

Sham
(Animal No. 3)

Vehicle Control
(Animal No. 14)

Compound 1 50mpk PO (Animal No. 40)

Compound 1 100mpk PO (Animal No. 47)

SUBSTITUTED CHROMENES FOR TREATMENT OF FIBROSIS OR NON-ALCOHOLIC STEATOHEPATITIS

BACKGROUND OF THE INVENTION

Field of the Invention present invention relates to a novel compound and a composition for the prevention, alleviation or treatment of fibrosis or non-alcoholic steatohepatitis, which contains the compound as an active ingredient, and more particularly to a novel compound of Formula 1, which has an excellent effect on the prevention, alleviation or treatment of fibrosis, and to a composition for the prevention, alleviation or treatment of fibrosis or non-alcoholic steatohepatitis, which contains the compound as an active ingredient.

Description of the Prior Art

Fibrosis is a disease in which excess fibrous connective tissue is formed in an organ or tissue in a reparative or reactive process. This fibrous connective tissue is as opposed to formation of normal fibrous tissue. When excess fibrous connective tissue is formed in an organ or tissue, the tissue becomes hard and the inflow of body fluids is reduced, so that its original function in vivo cannot be sufficiently performed. Fibrosis is known to be caused by injury, inflammation, burns, radiation, chemotherapy, lymphedema or the like. Problems associated with fibrosis vary depending on the location at which fibrous connective tissue is formed, and the liver, secretory organs, lungs and the like are mainly damaged by fibrosis. Typical examples of fibrosis include idiopathic pulmonary fibrosis (IPF), myelofibrosis, liver fibrosis and kidney fibrosis.

Currently known therapeutic agents against fibrosis include Pirfenidone (a therapeutic agent against idiopathic pulmonary fibrosis), Nintedanib (a therapeutic agent against idiopathic pulmonary fibrosis), Ruxolitinib (a therapeutic agent against myelofibrosis) and the like. However, there is a need to develop new therapeutic agents which are more effective, safe for the human body and easy to formulate.

Accordingly, the present inventor has conducted various studies related to fibrosis in order to a new therapeutic agent against fibrosis, and particularly paid attention on epithelial-mesenchymal transition (EMT) (hereinafter referred to as "EMT").

EMT refers to a phenomenon in which normal epithelial cells are genetically reprogrammed into mesenchymal cells whose morphology is likely to change, due to changes in the cytoskeleton in the intermediate stage while normal cells transform into tumor cells. Therefore, thinking that inhibition of EMT-related protein expression may inhibit tumor metastasis and proliferation, and thus many researchers have conducted studies related to EMT in order to develop tumor therapeutic agents. Several hundred regulators of EMT are known, including Twist, Snail, Slug, E-cadherin, vimentin, collagen11a1 and the like.

As described above, studies on EMT and regulators of the EMT have been conducted mostly for cancer or tumors. However, the present inventor has focused on the relationship between EMT and fibrosis based on some existing research results, and have expected that fibrosis can be prevented and treated if EMT can be regulated.

Accordingly, focusing on the relationship between EMT and fibrosis, the present inventor has conducted studies to develop a substance capable of effectively preventing, alleviating or treating fibrosis, and as a result, has found that a compound represented by Formula 1 as described in the specification exhibits an excellent effect on the prevention, alleviation or treatment of fibrosis by effectively regulating EMT and that non-alcoholic steatohepatitis can also be effectively alleviated or treated due to this effect, thereby completing the present invention.

SUMMARY OF THE INVENTION

Therefore, it is a main object of the present invention to provide a novel compound having an excellent effect on the prevention, alleviation or treatment of fibrosis.

Another object of the present invention is to provide a composition for the prevention, alleviation or treatment of fibrosis, which contains the compound as an active ingredient.

Still another object of the present invention is to provide a composition for the alleviation or treatment of non-alcoholic steatohepatitis, which contains the compound as an active ingredient.

In accordance with one aspect, the present invention provides a compound represented by the following Formula 1 or a pharmaceutically acceptable salt thereof:

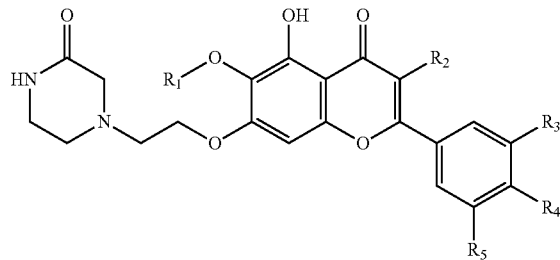

Formula 1 wherein $R_1$ is a substituted or unsubstituted $C_{1-5}$ linear or branched alkyl, a $C_{5-6}$ cycloalkyl, a $C_{5-6}$ cycloalkyl containing at least one heteroatom selected from among O and N, a substituted or unsubstituted $C_{6-12}$ aryl, or a $C_{5-6}$ heteroaryl containing at least one heteroatom selected from among O and N; $R_2$ is hydrogen, ethyl, acetyl, acetoxy, carboxy, benzoyloxy or 3,4,5-trihydroxybenzoyloxy; and $R_3$ to $R_5$ are each independently hydrogen, hydroxyl, methyl, methoxy, acetoxy, carboxy or benzoyloxy.

In accordance with another aspect, the present invention provides a pharmaceutical composition for the prevention or treatment of fibrosis, which contains the compound or a pharmaceutically acceptable salt thereof as an active ingredient.

In accordance with still another aspect, the present invention provides a food composition for the prevention or alleviation of fibrosis, which contains the compound or a pharmaceutically acceptable salt thereof as an active ingredient.

In accordance with still another aspect, the present invention provides a pharmaceutical composition for treatment of non-alcoholic steatohepatitis (NASH), which contains the compound or a pharmaceutically acceptable salt thereof as an active ingredient.

In accordance with yet another aspect, the present invention provides a food composition for alleviation of nonalcoholic steatohepatitis, which contains the compound or a pharmaceutically acceptable salt thereof as an active ingredient.

BRIEF DESCRIPTION OF THE DRAWINGS

FIGS. 22 to 24 show the results of examining the effects of comparative compounds for a compound of the present invention on cell fibrosis.

DETAILED DESCRIPTION OF THE INVENTION

Figure 1:
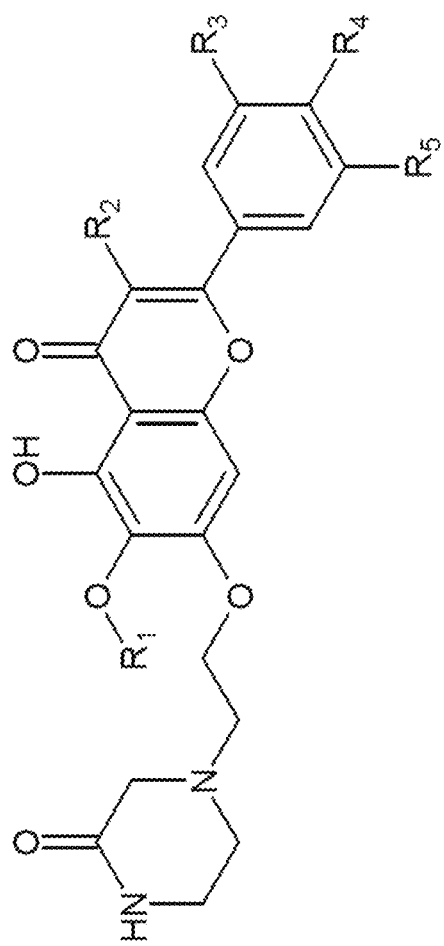
FIG. 1 shows a compound of the present invention.

The present invention provides a novel compound represented by the following Formula 1 or a pharmaceutically acceptable salt thereof:

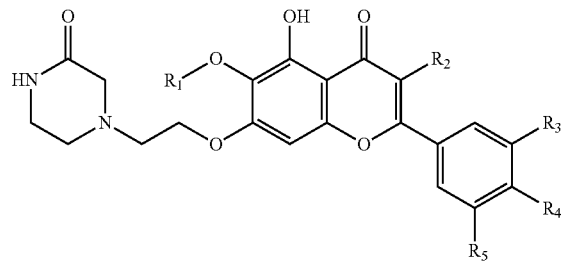

Formula 1 wherein $R_1$ is a substituted or unsubstituted $C_{1-5}$ linear or branched alkyl, a $C_{5-6}$ cycloalkyl, a $C_{5-6}$ cycloalkyl containing at least one heteroatom selected from among O and N, a substituted or unsubstituted $C_{6-12}$ aryl, or a $C_{5-6}$ heteroaryl containing at least one heteroatom selected from among O and N; $R_2$ is hydrogen, ethyl, acetyl, acetoxy, carboxy, benzoyloxy or 3,4,5-trihydroxybenzoyloxy; and $R_3$ to $R_5$ are each independently hydrogen, hydroxyl, methyl, methoxy, acetoxy, carboxy or benzoyloxy.

The novel compound or pharmaceutically acceptable salt thereof according to the present invention can prevent, alleviate or treat fibrosis.

The compound or pharmaceutically acceptable salt thereof according to the present invention can inhibit cell fibrosis by inhibiting expression of important factors such as α-SMA (alpha-smooth muscle actin), Snail and Vimentin, which are involved in EMT (epithelial-mesenchymal transition).

Due to this effect, the compound or pharmaceutically acceptable salt thereof according to the present invention can prevent, alleviate or treat fibrosis which is a disease in which cells in an organ or tissue become fibrous by any cause.

Furthermore, nonalcoholic steatohepatitis (NASH) is also a disease in which fibrosis of liver cells occurs. Thus, the novel compound or pharmaceutically acceptable salt thereof according to the present invention can alleviate or treat this nonalcoholic steatohepatitis.

In particular, the compound or pharmaceutically acceptable salt thereof according to the present invention can strongly inhibit the growth and fibrosis of cells already programmed to become fibrous and can restore these cells into normal cells. This effect means that a state in which fibrosis has progressed can be restored into a normal state, supporting that the compound or pharmaceutically acceptable salt thereof according to the present invention can exhibit a strong effect on the treatment of fibrosis.

The compound or pharmaceutically acceptable salt thereof according to the present invention is neither easily degraded by liver microsomes nor transferred to other materials, and thus can exhibit a long-lasting effect while maintaining its original structure in vivo. Furthermore, it is advantageous for formulation because the solubility thereof in phosphate buffer which is generally used is not low. Moreover, it is safe for the human body because the inhibitory activity thereof against CYP450 is low. In addition, it has a very high administration easiness because it can be absorbed rapidly in vivo even after oral administration.

For the fibrosis inhibitory effect, in vivo stability, safety for the human body and the like as described above, $R_1$ in the compound or pharmaceutically acceptable salt thereof according to the present invention is preferably methyl, ethyl, cyclopentyl, cyclohexyl, phenyl or benzyl. More preferably, $R_1$ is methyl. In addition, preferably, $R_2$ is hydrogen, $R_4$ is hydroxy or methoxy, and $R_3$ and $R_5$ are each independently hydrogen, hydroxy or methoxy. More preferably, the compound or pharmaceutically acceptable salt thereof according to the present invention is a compound represented by any one of the following Formulas 2 to 5 or a pharmaceutically acceptable salt thereof:

Formula 2

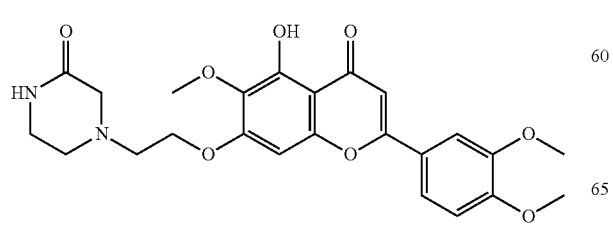

Formula 3

Formula 4

Formula 5

The compound of the present invention may be prepared by the method shown in the following Reaction Schemes 1 and 2:

Reaction Scheme 1

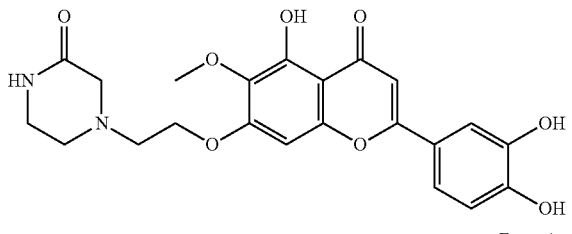

-continued
Reaction Scheme 2

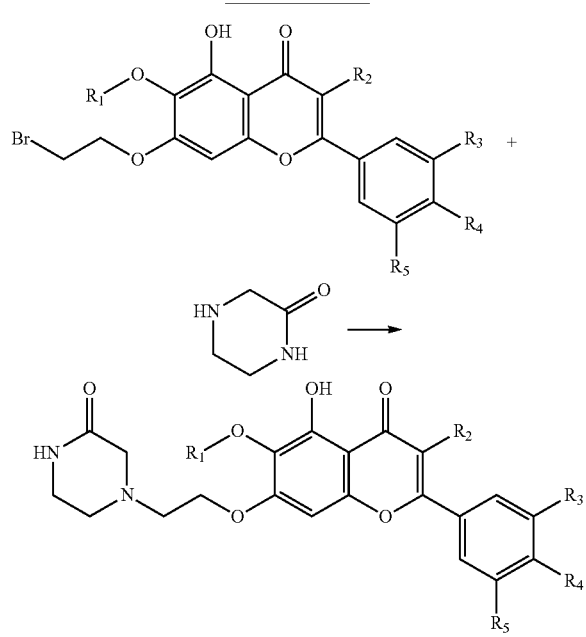

wherein $R_1$ to $R_5$ correspond to $R_1$ to $R_5$ of Formula 1.

Based on the above-described effect, the present invention provides a pharmaceutical composition for the prevention or treatment of fibrosis, which contains the compound or a pharmaceutically acceptable salt thereof as an active ingredient.

In this regard, the fibrosis is preferably any one selected from the group consisting of idiopathic pulmonary fibrosis, myelofibrosis, liver fibrosis and kidney fibrosis.

The present invention also provides a food composition for the prevention or alleviation of fibrosis, which contains the compound or a pharmaceutically acceptable salt thereof as an active ingredient.

In this regard, the fibrosis is preferably any one selected from the group consisting of idiopathic pulmonary fibrosis, myelofibrosis, liver fibrosis and kidney fibrosis.

The present invention also provides a pharmaceutical composition for treatment of non-alcoholic steatohepatitis (NASH), which contains the compound or a pharmaceutically acceptable salt thereof as an active ingredient.

The present invention also provides a food composition for alleviation of non-alcoholic steatohepatitis (NASH), which contains the compound or a pharmaceutically acceptable salt thereof as an active ingredient.

The pharmaceutical composition of the present invention may be a composition containing the compound or pharmaceutically acceptable salt thereof according to the present invention alone or in combination with a pharmaceutically acceptable carrier.

It is believed that the pharmaceutical composition of the present invention may contain the compound or pharmaceutically acceptable salt thereof according to the present invention in an amount of 0.0001 to 100 wt % based on the total weight of the composition.

It is believed that the pharmaceutical composition of the present invention may be administered orally or parenterally in clinical practice. For parenteral administration, the pharmaceutical composition may be administered by intraperitoneal injection, intrarectal injection, subcutaneous injection, intravenous injection, intramuscular injection, intrauterine dural injection, intracerebrovascular injection or intrathoracic injection, and may be used as a general drug formulation.

The pharmaceutical composition of the present invention may be used alone or in combination with surgery, radiotherapy, hormonal therapy, chemotherapy and other methods employing biological reaction regulators.

The daily dose of the compound or pharmaceutically acceptable salt thereof contained in the pharmaceutical composition of the present invention may be about 0.0001 g to 100 mg/kg/day, preferably 0.001 g to 10 mg/kg/day, on the basis of in the composition, and may be administrated once or several times a day, with the range thereof being variable depending on patient's weight, age, sex, health condition, diet, administration time, administration mode, excretion rate, and severity of the disease.

For oral or parenteral administration in clinical practice, the pharmaceutical composition may be formulated in various forms by using diluents or excipients, including fillers, extenders, binders, wetting agents, disintegrants, surfactants and the like, which are generally used.

In particular, the compound of the present invention can be absorbed rapidly in vivo even after oral administration. In view of bioavailability and in vivo stability, the compound of the present invention is preferably formulated using NMP (N-methyl-2-pyrrolidone), PEG400, SOLUTOL HS and water or formulated using HPCD (hydroxypropyl-beta-cyclodextrin). In this regard, the ratio of NMP:PEG400:SOLUTOL HS:water is preferably 5-15:10-30:10-30:40-60 (v/v), more preferably 8-12:15-25:15-25:45-55 (v/v). Where the compound of the present invention is formulated using HPCD, a method of dissolving the compound in 10-50% (w/v) HPCD aqueous solution is preferably used. More preferably, 20-40% (w/v) HPCD aqueous solution is used.

When the compound of the present invention, formulated with HPCD as described above, is orally administered for the purpose of preventing, alleviating or treating fibrosis, may preferably be administered at a dose of 1 to 50 mg/kg/day, more preferably 5 to 20 mg/kg/day, for mice, and may preferably be administered at a dose of 0.08 to 4 mg/kg/day, more preferably 0.4 to 1.6 mg/kg/day, for humans.

In addition, the compound of the present invention may also be formulated using CMC (carboxymethyl cellulose) and Tween80 such that the concentration of CMC is 0.1 to 1% (w/v) and the concentration of Tween80 is 0.1 to 2%. When the compound of the present invention, formulated with CMC and Tween80 as described above, is orally administered for the purpose of preventing, alleviating or treating non-alcoholic steatohepatitis, it may preferably be administered at a dose of 1 to 70 mg/kg/day, more preferably 5 to 60 mg/kg/day, for rats, and may preferably be administered at a dose of 0.16 to 11.4 mg/kg/day, more preferably 0.8 to 9.7 mg/kg/day, for humans.

The pharmaceutical composition of the present invention may contain, in addition to the compound or pharmaceutically acceptable salt thereof according to the present invention, at least one active ingredient showing the same or similar function.

The food composition of the present invention may be a composition containing the compound or pharmaceutically acceptable salt thereof according to the present invention alone or in combination with a food-acceptable carrier. In this case, the content of the compound or pharmaceutically acceptable salt thereof according to the present invention may be suitably controlled according to a conventional method based on the content thereof in the pharmaceutical composition and the dose thereof. It is believed that the food composition of the present invention may be in the form of processed meat products, fish meat products, Tofu, Muk (jellied food), porridge, noodles such as ramen noodles, seasonings such as soy sauce, soybean paste, red pepper paste, mixed soybean paste or the like, sauces, confectionery, dairy products such as fermented milk, cheese or the like, pickled foods such as kimchi, pickled vegetables or the like, or drinks such as fruit drinks, vegetable drinks, soy milk, fermented drinks or the like. In addition, the food-acceptable carrier may also be the pharmaceutically acceptable carrier as described above.

Hereinafter, the present invention will be described in more detail with reference to examples and experimental examples. It is to be understood, however, that these examples and experimental examples are for illustrative purposes only and are not intended to limit the scope of the present invention.

Example 1: Synthesis of Compound of the Present Invention 1-1: Synthesis of 7-(benzyloxy)-5-hydroxy-2-phenyl-4H-chromen-4-one (Precursor Compound 2) (Step-1)

Figure 2:
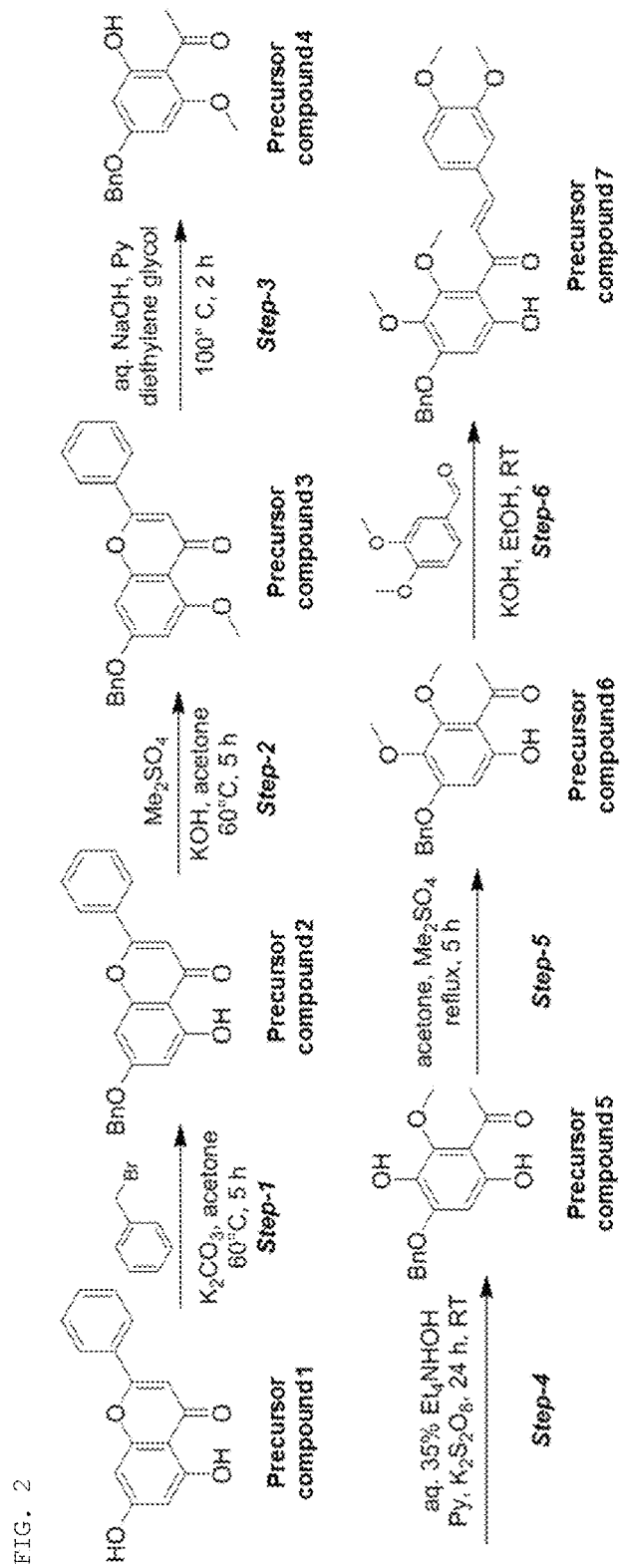
FIGS. 2 and 3 show a process of synthesizing a compound of the present invention according to one example of the present invention.

This step is a step of performing step-1 shown in FIG. 2, and the detailed description thereof is as follows.

To a stirred suspension of 5,7-dihydroxy-2-phenyl-4H-chromen-4-one (precursor compound 1) (75 g; 0.294 mol; 1 equiv) in acetone (700 mL) was added potassium carbonate (121.8 g; 0.442 mol; 3.0 equiv) and benzyl bromide (75.5 g; 0.442 mol; 1.5 equiv) in drops at 0° C. The reaction mixture was warmed to room temperature and then heated at 60° C. for 5 h. The reaction completion was confirmed by TLC (8:2/PE:EtOAc; $R_f$~0.5). The mixture was allowed to cool to room temperature and $K_2CO_3$ was removed by filtration and the cake was washed with DCM several times until there was no product was intact. The combined filtrate was concentrated to dryness and the resulted solid was slurred with diethyl ether (200 mL), filtered and dried under suction to afford 7-(benzyloxy)-5-hydroxy-2-phenyl-4H-chromen-4-one (precursor compound 2) as yellow solid (yield: 90.0 g; 88.6%).

Figure 4:
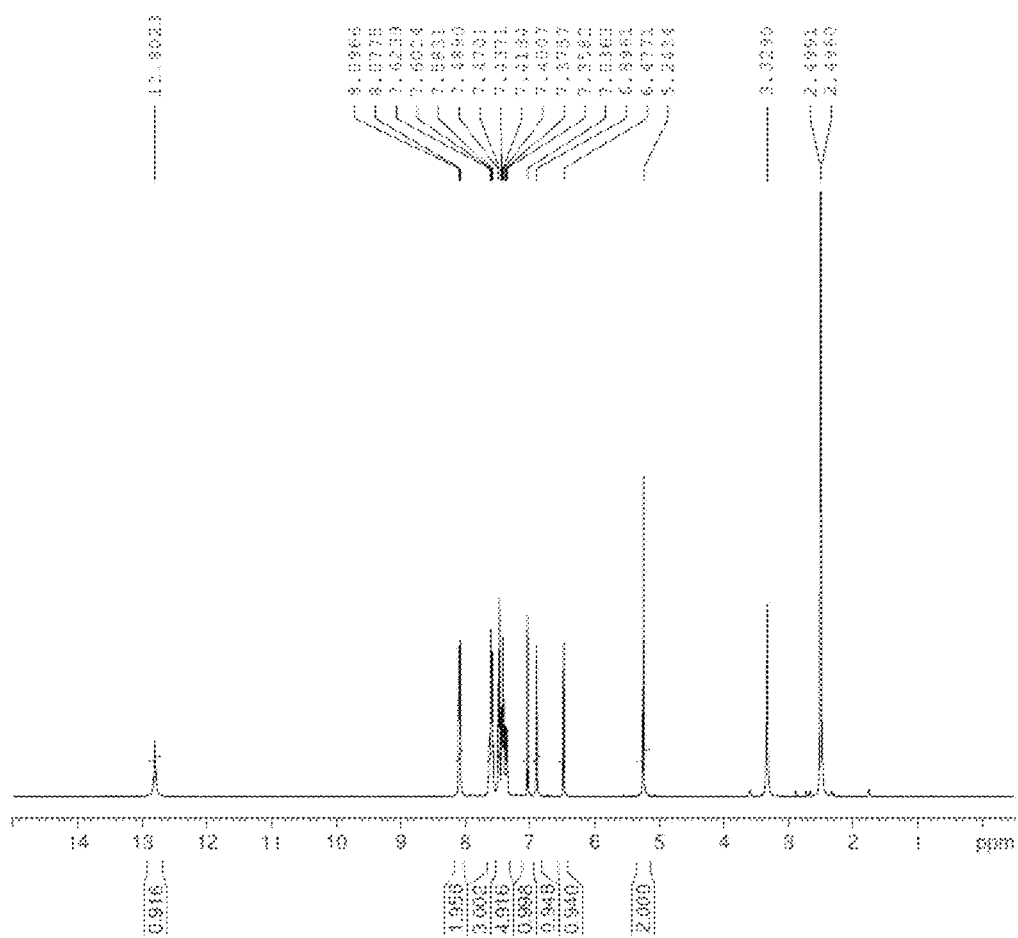
FIG. 4 shows the results of LCMS-NMR analysis of 7-(benzyloxy)-5-hydroxy-2-phenyl-4H-chromen-4-one produced in a process of synthesizing a compound of the present invention according to one example of the present invention.

The obtained 7-(benzyloxy)-5-hydroxy-2-phenyl-4H-chromen-4-one (precursor compound 2) was analyzed by LCMS-NMR under the following conditions, and the results are shown in FIG. 4.

LCMS: Mass found; (345.0; M+1).
Method: A—0.1% HCOOH in $H_2O$, B: ACN; Flow Rate: 1.5 mL/min; +ve mode.
Column: Zorbax extended C18 (50×4.6 mm, 5 μm).
Rt (min): 3.46; Area %—97.97.
$^1$H-NMR (400 MHz, DMSO-$d_6$): δ 12.83 (s, 1H), 8.10-8.12 (m, 2H), 7.62-7.65 (m, 3H), 7.51-7.62 (m, 2H), 7.43-7.50 (m, 2H), 7.38-7.41 (m, 3H), 7.06 (s, 1H), 6.93 (s, 1H), 6.51 (d, J=2.40 Hz, 1H), 5.27 (s, 2H).

1-2. Synthesis of 7-(benzyloxy)-5-methoxy-2-phenyl-4H-chromen-4-one (Precursor Compound 3) (Step-2)

This step is a step of performing step-2 shown in FIG. 2, and the detailed description thereof is as follows.

To a stirred suspension of 7-(benzyloxy)-5-hydroxy-2-phenyl-4H-chromen-4-one (precursor compound 2) (90 g; 0.261 mol; 1 equiv) in acetone (900 mL) was added solid. KOH (43.9 g; 0.784 mol; 3 equiv) at room temperature. The reaction mixture was warmed to 60° C. and added dimethyl sulfate (37.1 mL; 0.392 mol; 1.5 equiv) dropwise at 60° C. The reaction mixture was stirred at 60° C. for 5 h. The reaction completion was determined by TLC (1:1/PE:EtOAc; $R_f$~0.2). The mixture was allowed to cool to room temperature and acidified with 10% aq. HCl solution until pH was adjusted to 2. The resulted precipitate was collected by filtration and washed with water, dried under suction for 12 h to afford 7-(benzyloxy)-5-methoxy-2-phenyl-4H-chromen-4-one (precursor compound 3) as yellow solid (yield: 90 g; 96%).

Figure 5:
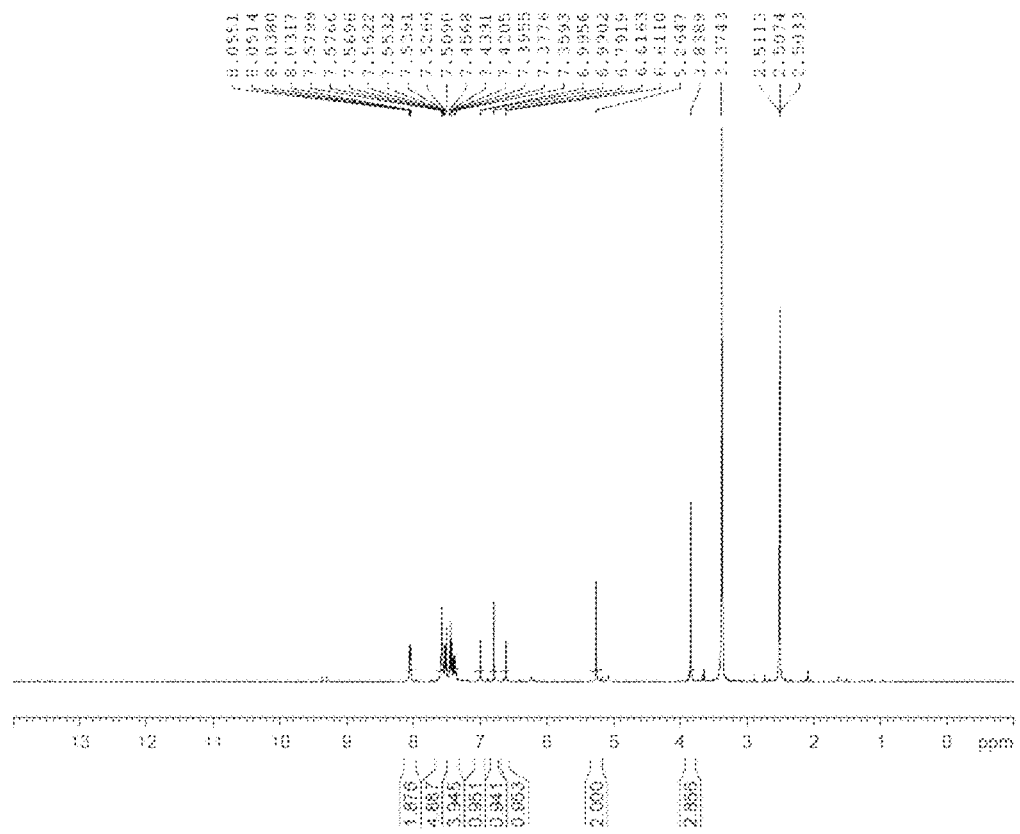
FIG. 5 shows the results of LCMS-NMR analysis of 7-(benzyloxy)-5-methoxy-2-phenyl-4H-chromen-4-one produced in a process of synthesizing a compound of the present invention according to one example of the present invention.

The obtained 7-(benzyloxy)-5-methoxy-2-phenyl-4H-chromen-4-one (precursor compound 3) was analyzed by LCMS-NMR under the following conditions, and the results are shown in FIG. 5.

LCMS: Mass found; (359.0; M+1).
Method: A—0.1% HCOOH in $H_2O$, B: ACN; Flow Rate: 1.5 mL/min; +ve mode;
Column: Zorbax extended C18 (50×4.6 mm, 5 μm).
Rt (min): 2.94; Area %—97.85.
$^1$H-NMR (400 MHz, DMSO-$d_6$): δ 8.04-8.06 (m, 2H), 7.46-7.58 (m, 5H), 7.38-7.44 (m, 3H), 7.00 (d, J=2.00 Hz, 1H), 6.80 (d, J=1.60 Hz, 1H), 6.62 (d, J=2.00 Hz, 1H), 5.27 (s, 2H), 3.83 (s, 3H).

1-3: Synthesis of 1-(4-(benzyloxy)-2-hydroxy-6-methoxyphenyl)ethan-1-one (Precursor Compound 4) (Step-3)

This step is a step of performing step-3 shown in FIG. 2, and the detailed description thereof is as follows.

To a stirred suspension of 7-(benzyloxy)-5-methoxy-2-phenyl-4H-chromen-4-one (precursor compound 3) (90 g; 0.251 mol; 1 equiv) in aqueous sodium hydroxide solution (50%; 686 mL; 8.79 mol; 35 equiv) was added pyridine (417.1 mL; 5.02 mol; 20 equiv) at room temperature. The dark brown mixture was vigorously stirred and treated with diethylene glycol (475 mL, 5.02 mol, 20 equiv) in drops. The mixture was heated to 100° C. and stirred for 2 h. The reaction completion was confirmed by TLC (1:1/PE:EtOAc; $R_f$~0.5). The mixture was cooled to 0° C. and the pH was adjusted to 1 with 12N aqueous hydrochloric acid solution. The aqueous portion was extracted with ethyl acetate (2×500 mL). The combined organic phase was washed with saturated aqueous sodium bicarbonate solution, water and brine solution. Dried with sodium sulfate, and the solvent was removed under reduced pressure. The resulted residue was re dissolved in diethyl ether (700 mL) and the insoluble dark particles were removed by filtration. The filtrate was concentrated in vacuum to afford 1-(4-(benzyloxy)-2-hydroxy-6-methoxyphenyl)ethan-1-one (precursor compound 4) as pale yellow solid (yield: 70 g; 97%).

Figure 6:
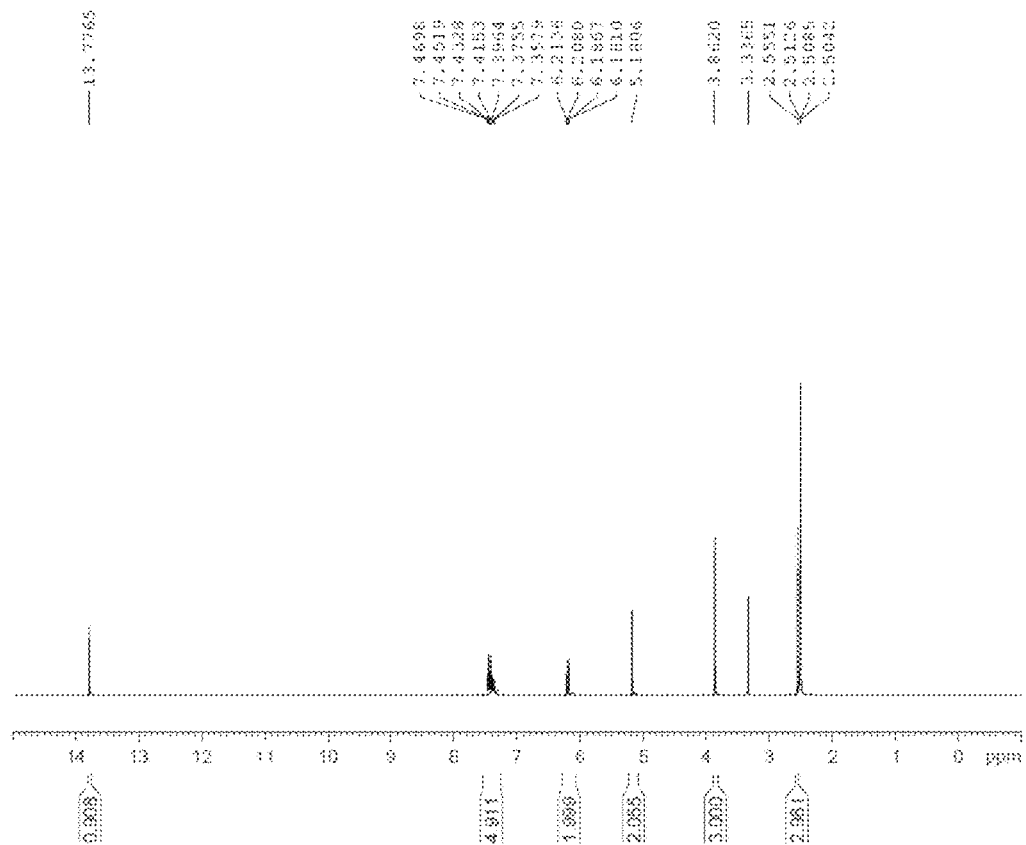
FIG. 6 shows the results of LCMS-NMR analysis of 1-(4-(benzyloxy)-2-hydroxy-6-methoxyphenyl)ethan-1-one produced in a process of synthesizing a compound of the present invention according to one example of the present invention.

The obtained 1-(4-(benzyloxy)-2-hydroxy-6-methoxyphenyl)ethan-1-one (precursor compound 4) was analyzed by LCMS-NMR under the following conditions, and the results are shown in FIG. 6.

LCMS: Mass found; (273.0; M+1).
Method: A—0.1% HCOOH in $H_2O$, B: ACN; Flow Rate: 1.5 mL/min; +ve mode.
Column: Zorbax extended C18 (50×4.6 mm, 5 μm).
Rt (min): 3.15; Area %—93.79.
$^1$H-NMR (400 MHz, DMSO-$d_6$): δ 13.77 (s, 1H), 7.35-7.47 (m, 5H), 6.18-6.21 (d, 2H), 5.18 (s, 2H), 3.86 (s, 3H), 2.51 (s, 3H).

1-4: Synthesis of 1-(4-(benzyloxy)-3,6-dihydroxy-2-methoxyphenyl)ethan-1-one (Precursor Compound 5) (Step-4)

This step is a step of performing step-4 shown in FIG. 2, and the detailed description thereof is as follows.

To a stirred suspension of 1-(4-(benzyloxy)-2-hydroxy-6-methoxyphenyl)ethan-1-one (precursor compound 4) (30 g; 0.110 mol; 1 equiv) in aq. tetraethyl ammonium hydroxide solution (35%; 632 mL; 1.43 mol; 13 equiv) was added pyridine (69.4 mL; 0.0.836 mol; 7.6 equiv) in drops. The reaction mixture became clear dark solution. In a separate flask, potassium persulfate (50.49 g; 0.187 mol; 1.7 equiv) in water (1 L) was taken and to this solution, the above reaction mixture was added in drops at room temperature and continued to stir for another 24 h. After confirming the consumption of starting material by TLC, conc. HCl was added to the reaction mixture to adjust the pH to 1-2 at 0° C. The resulted brownish gummy residue was passed through filtration and the aq. filtrate was further washed with diethyl ether (1×100 mL).

The separated aqueous layer was treated with sodium sulfite (11.09 g; 0.0.088 mol; 0.8 equiv), con HCl (110 mL) and benzene (220 mL). This reaction mixture was heated to 95° C. for 1 h. The reaction completion was determined by TLC (8:2/PE:EtOAc; $R_f$~0.3). The reaction mixture was cooled to 0° C. and extracted with ethyl acetate (2×300 mL). The combined organic phase was washed with brine solution, dried with sodium sulfate and the solvent was removed under reduced pressure. The residue was purified by column chromatography over silica gel (60-120 mesh) eluting with ethyl acetate (10-12%) in pet ether as an eluent to afford 1-(4-(benzyloxy)-3,6-dihydroxy-2-methoxyphenyl)ethan-1-one (precursor compound 5) as yellow solid (yield: 10 g; 31%).

Figure 7:
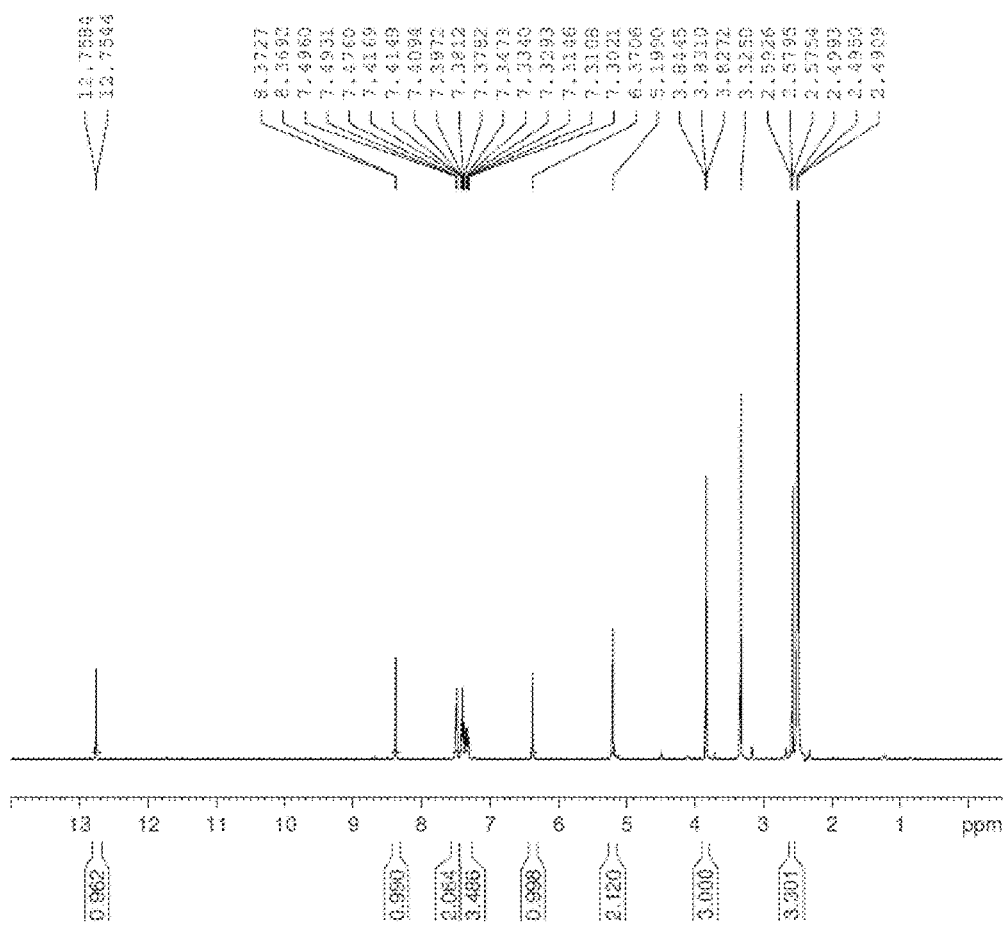
FIG. 7 shows the results of LCMS-NMR analysis of 1-(4-(benzyloxy)-3,6-dihydroxy-2-methoxyphenyl)ethane-1-one produced in a process of synthesizing a compound of the present invention according to one example of the present invention.

The obtained 1-(4-(benzyloxy)-3,6-dihydroxy-2-methoxyphenyl)ethan-1-one (precursor compound 5) was analyzed by LCMS-NMR under the following conditions, and the results are shown in FIG. 7.

LCMS: Mass found; (289.0; M+1).
Method: A—0.1% HCOOH in $H_2O$, B: ACN; Flow Rate: 1.5 mL/min; +ve mode.
Column: Zorbax extended C18 (50×4.6 mm, 5 μm).
Rt (min): 2.68; Area %—91.01.
$^1$H-NMR (400 MHz, DMSO-$d_6$): δ 12.76 (s, 1H), 8.37 (s, 1H), 7.41-7.51 (m, 2H), 7.31-7.38 (m, 3H), 6.38 (s, 1H), 5.21 (s, 2H), 3.84 (s, 3H), 2.51 (s, 3H).

1-5: Synthesis of 1-(4-(benzyloxy)-6-hydroxy-2,3-dimethoxyphenyl)ethan-1-one (Precursor Compound 6) (Step-5)

This step is a step of performing step-5 shown in FIG. 2, and the detailed description thereof is as follows.

To a stirred suspension of 1-(4-(benzyloxy)-3,6-dihydroxy-2-methoxyphenyl)ethan-1-one (precursor compound 5) (28 g; 0.097 mol; 1 equiv) in acetone (300 mL) was added $K_2CO_3$ (20 g; 0.145 mol; 1.5 equiv) at RT. The reaction mixture was warmed to 60° C. and then added dimethyl sulfate (18.2 mL; 0.145 mol; 2 equiv) dropwise at 60° C. The reaction mixture was stirred at 60° C. for 5 h. After confirming the reaction completion by TLC, the mixture was allowed to cool to room temperature and $K_2CO_3$ was removed by filtration and the cake was washed with DCM several times until there was no product remain. The combined filtrate was concentrated to dryness and the resulted residue was purified by column chromatography over silica gel (60-120 mesh) eluting with ethyl acetate (8-10%) in pet ether as an eluent to afford 1-(4-(benzyloxy)-6-hydroxy-2,3-dimethoxyphenyl)ethan-1-one (precursor compound 6) as white solid (yield: 25 g; 85%).

Figure 8:
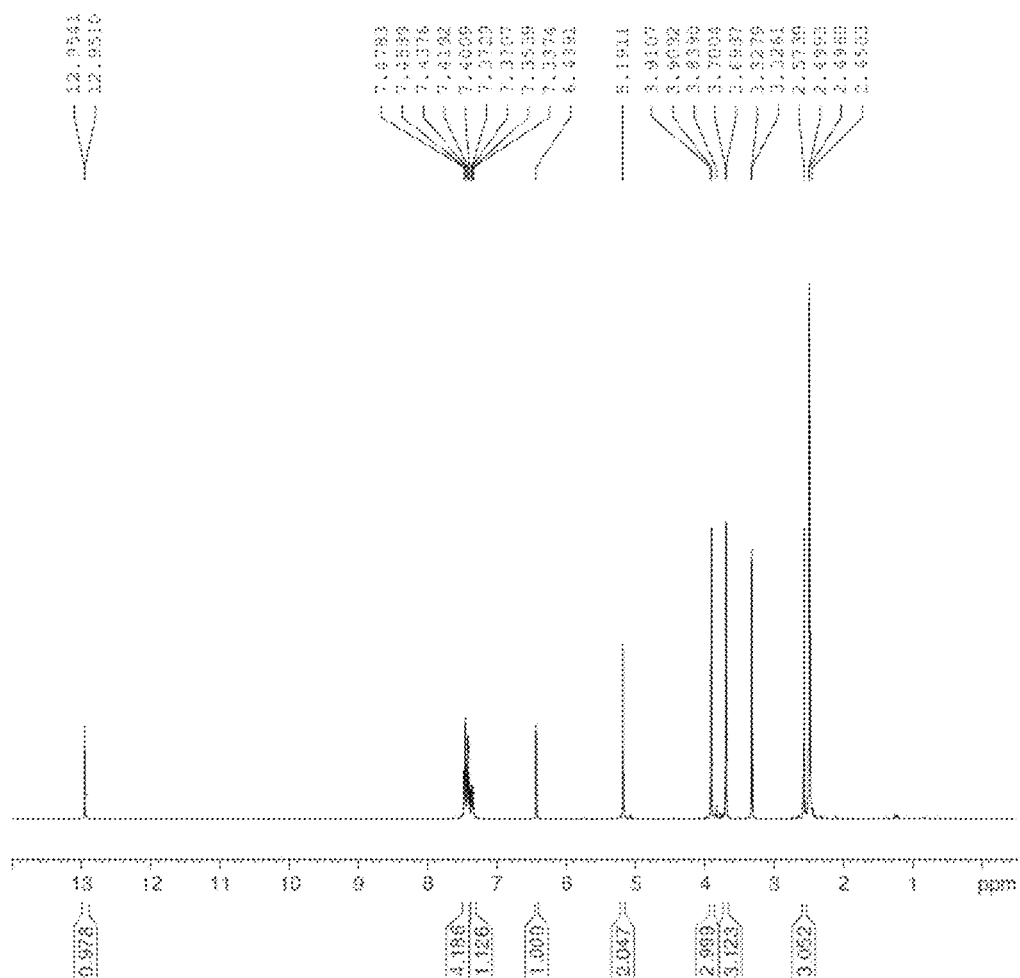
FIG. 8 shows the results of LCMS-NMR analysis of 1-(4-(benzyloxy)-6-hydroxy-2,3-dimethoxyphenyl)ethan-1-one produced in a process of synthesizing a compound of the present invention according to one example of the present invention.

The obtained 1-(4-(benzyloxy)-6-hydroxy-2,3-dimethoxyphenyl)ethan-1-one (precursor compound 6) was analyzed by LCMS-NMR under the following conditions, and the results are shown in FIG. 8.

LCMS: Mass found; (303.0; M+1).
Method: A—0.1% HCOOH in $H_2O$, B: ACN; Flow Rate: 1.5 mL/min; +ve mode.
Column: Zorbax extended C18 (50×4.6 mm, 5 μm).
Rt (min): 3.11; Area %—99.85.
$^1$H-NMR (400 MHz, DMSO-$d_6$): δ 12.95 (s, 1H), 7.36-7.48 (m, 5H), 6.45 (s, 1H), 5.20 (s, 2H), 3.96 (s, 3H), 3.92 (s, 3H), 2.51 (s, 3H).

1-6: Synthesis of (E)-1-(4-(benzyloxy)-6-hydroxy-2,3-dimethoxyphenyl)-3-(3,4-dimethoxyphenyl)prop-2-en-1-one (Precursor Compound 7) (Step-6)

This step is a step of performing step-6 shown in FIG. 2, and the detailed description thereof is as follows.

To a stirred suspension of 1-(4-(benzyloxy)-6-hydroxy-2,3-dimethoxyphenyl)ethan-1-one (precursor compound 6) (25 g; 0.082 mol; 1 equiv) and 3,4-dimethoxybenzaldehyde (16.4 g; 0.099 mol; 1.2 equiv) in ethanol (200 mL) was added solution of KOH (46 g; 0.0.82 mol; 1 equiv) in water at room temperature. The reaction mixture was stirred at room temperature for 24 h. TLC (6:4/PE:EtOAc; $R_f$ 0.4) confirmed that 70-75% product formation and the unreacted starting materials were intact after 24 h. The mixture was concentrated in vacuum and the residue was partitioned between aq. sodium bisulfate and DCM. The separated organic phase was washed with water, brine solution and dried with sodium sulfate. Concentrated under vacuum and the resulted residue was slurred with diethyl ether (100 mL), filtered and dried under suction to obtain (E)-1-(4-(benzyloxy)-6-hydroxy-2,3-dimethoxyphenyl)-3-(3,4-dimethoxyphenyl)prop-2-en-1-one (precursor compound 7) as yellow solid (yield: 23.0 g; 39%).

Figure 9:
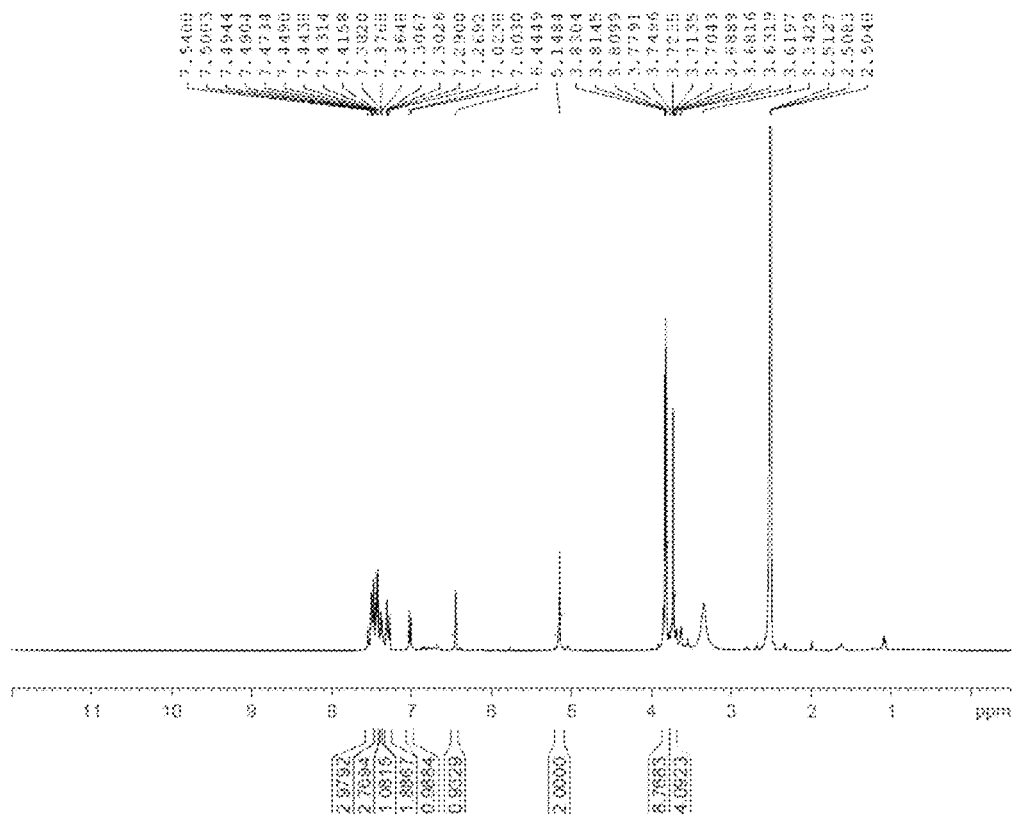
FIG. 9 shows the results of LCMS-NMR analysis of (E)-1-(4-(benzyloxy)-6-hydroxy-2,3-dimethoxyphenyl)-3-(3,4-dimethoxyphenyl)prop-2-en-1-one produced in a process of synthesizing a compound of the present invention according to one example of the present invention.

The obtained (E)-1-(4-(benzyloxy)-6-hydroxy-2,3-dimethoxyphenyl)-3-(3,4-dimethoxyphenyl)prop-2-en-1-one (precursor compound 7) was analyzed by LCMS-NMR under the following conditions, and the results are shown in FIG. 9.

LCMS: Mass found; (450.9; M+1).
Method: A—0.1% HCOOH in $H_2O$, B: ACN; Flow Rate: 1.5 mL/min; +ve mode.
Column: Zorbax extended C18 (50×4.6 mm, 5 μm).
Rt (min): 3.34; Area %—98.16.
$^1$H-NMR (400 MHz, DMSO-$d_6$): δ 11.96 (s, 1H), 7.49-7.57 (m, 3H), 7.49-7.57 (m, 4H), 7.29-7.39 (m, 2H), 7.03 (d, J=8.40 Hz, 1H), 6.47 (s, 1H), 5.19 (s, 2H), 3.85 (s, 3H), 3.83 (s, 3H), 3.77 (s, 3H), 3.74 (s, 3H).

1-7: Synthesis of 5-(benzyloxy)-2-(3,4-dimethoxyphenyl)-6,7-dimethoxy-4H-chromen-4-one (Precursor Compound 8) (Step-7)

Figure 3:
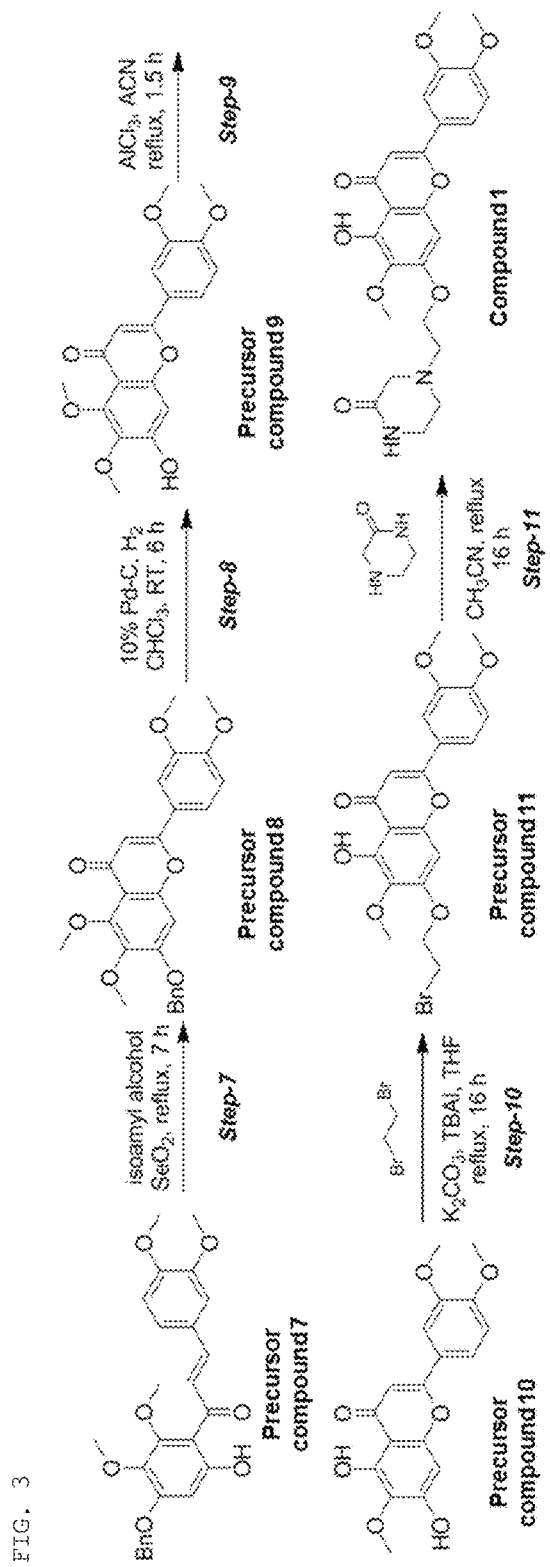

This step is a step of performing step-7 shown in FIG. 3, and the detailed description thereof is as follows.

To a stirred suspension of (E)-1-(4-(benzyloxy)-6-hydroxy-2,3-dimethoxyphenyl)-3-(3,4-dimethoxyphenyl) prop-2-en-1-one (precursor compound 7) (21 g; 0.0466 mol; 1 equiv) in isoamyl alcohol (300 mL) was added selenium dioxide (21 g; 0.466 mol; 10 equiv) at room temperature.

The mixture was heated to 140° C. and stirred for 7 h. After confirming the reaction completion by TLC (4:6/PE:EtOAc; $R_f$~0.2), the mixture was allowed to cool to room temperature and the resulted dark particles were removed by filtration on celite pad. The pad was washed with DCM and the filtrate was concentrated under vacuum. The resulted residue was diluted with DCM (500 mL), washed with aq. $NaHCO_3$ solution, water and brine. Dried with sodium sulfate and the solvent was removed under reduced pressure The residue was purified by column chromatography over silica gel (60-120 mesh) eluting with ethyl acetate (50-60%) in pet ether as an eluent to afford 5-(benzyloxy)-2-(3,4-dimethoxyphenyl)-6,7-dimethoxy-4H-chromen-4-one (precursor compound 8) as yellow solid (yield: 16 g; 76%).

Figure 10:
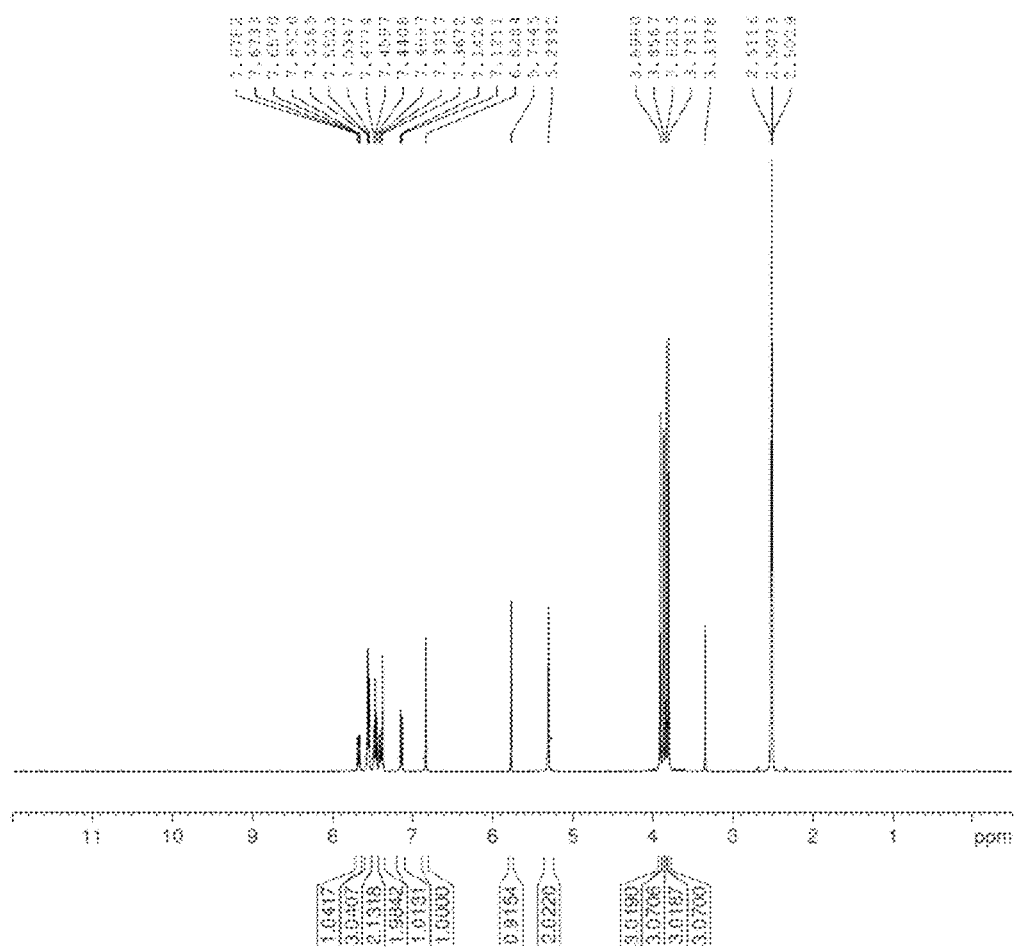
FIG. 10 shows the results of LCMS-NMR analysis of 5-(benzyloxy)-2-(3,4-dimethoxyphenyl)-6,7-dimethoxy-4H-chromen-4-one produced in a process of synthesizing a compound of the present invention according to one example of the present invention.

The obtained 5-(benzyloxy)-2-(3,4-dimethoxyphenyl)-6,7-dimethoxy-4H-chromen-4-one (precursor compound 8) was analyzed by LCMS-NMR under the following conditions, and the results are shown in FIG. 10.

LCMS: Mass found; (449.0; M+1).
Method: A—0.1% HCOOH in $H_2O$, B: ACN; Flow Rate: 1.5 mL/min; +ve mode.
  Column: Zorbax extended C18 (50×4.6 mm, 5 μm).
  Rt (min): 2.83; Area %—98.62.
  1H-NMR (400 MHz, DMSO-$d_6$): δ 7.54 (d, J=8.40 Hz, 1H), 7.45 (t, J=7.60 Hz, 2H), 7.37 (d, J=8.40 Hz, 2H), 7.13 (d, J=8.80 Hz, 2H), 6.82 (s, 1H), 5.30 (s, 2H), 3.89 (s, 3H), 3.85 (s, 3H), 3.82 (s, 3H), 3.77 (s, 3H).

1-8: Synthesis of 2-(3,4-dimethoxyphenyl)-7-hydroxy-5,6-dimethoxy-4H-chromen-4-one (Precursor Compound 9) (Step-8)

This step is a step of performing step-8 shown in FIG. 3, and the detailed description thereof is as follows.

To a stirred solution of 5-(benzyloxy)-2-(3,4-dimethoxyphenyl)-6,7-dimethoxy-4H-chromen-4-one (precursor compound 8) (19 g; 0.0424 mol; 1 equiv) in chloroform (200 mL) was added 10% Pd/C (3.8 g) and the mixture was hydrogenated under ballon atmosphere at room temperature for 6-7 h. After the reaction was completed by TLC, the catalyst was filtered through celite pad. The pad was washed with 20% MeOH in DCM and the combined filtrate was concentrated in vacuum to afford dark brown solid. The solid was triturated with ethyl acetate (80 mL), filtered and dried under suction to obtain 2-(3,4-dimethoxyphenyl)-7-hydroxy-5,6-dimethoxy-4H-chromen-4-one (precursor compound 9) as yellow solid (yield: 11.0 g; 72%).

Figure 11:
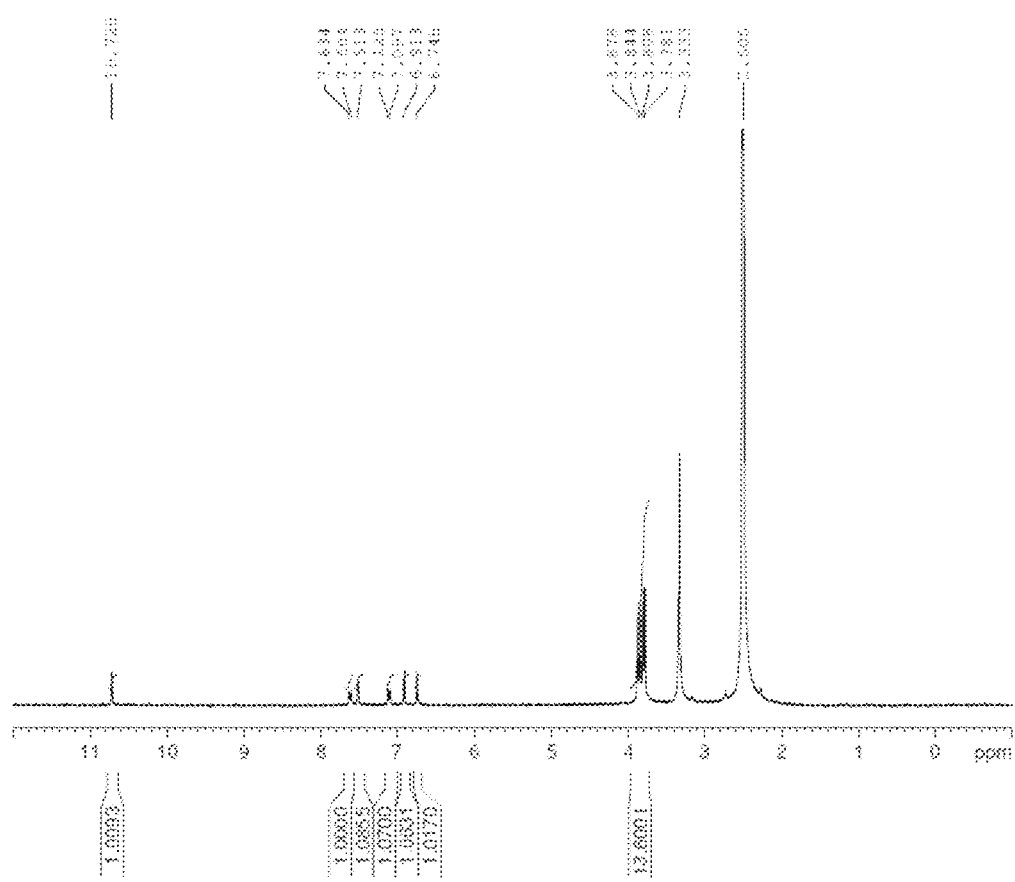
FIG. 11 shows the results of LCMS-NMR analysis of 2-(3,4-dimethoxyphenyl)-7-hydroxy-5,6-dimethoxy-4H-chromen-4-one produced in a process of synthesizing a compound of the present invention according to one example of the present invention.

The obtained 2-(3,4-dimethoxyphenyl)-7-hydroxy-5,6-dimethoxy-4H-chromen-4-one (precursor compound 9) was analyzed by LCMS-NMR under the following conditions, and the results are shown in FIG. 11.

LCMS: Mass found; (359.0; M+1).
Method: A—0.1% HCOOH in $H_2O$, B: ACN; Flow Rate: 1.5 mL/min; +ve mode.
  Column: Zorbax extended C18 (50×4.6 mm, 5 μm).
  Rt (min): 2.07; Area %—99.63.
  $^1$H-NMR (400 MHz, DMSO-$d_6$): δ 10.69 (s, 1H), 7.61 (d, J=8.40 Hz, 1H), 7.51 (s, 1H), 7.11 (d, J=8.40 Hz, 1H), 6.90 (s, 1H), 6.74 (s, 1H), 3.87 (s, 3H), 3.84 (s, 3H), 3.80 (s, 3H), 3.77 (s, 3H).

1-9: Synthesis of 2-(3,4-dimethoxyphenyl)-5,7-dihydroxy-6-methoxy-4H-chromen-4-one (Precursor Compound 10) (Step-9)

This step is a step of performing step-9 shown in FIG. 3, and the detailed description thereof is as follows.

To a stirred solution of 2-(3,4-dimethoxyphenyl)-7-hydroxy-5,6-dimethoxy-4H-chromen-4-one (precursor compound 9) (11 g; 0.0307 mol; 1 equiv) in acetonitrile (100 mL) was added $AlCl_3$ (20.3 g; 0.153 mol; 5 equiv) in portions at room temperature and then the mixture was refluxed at 90° C. for 2 h. The reaction completion was determined by TLC and the solvent was evaporated to dryness. The resulted residue was treated with aq. HCl (10%; 200 mL) and chloroform (200 mL) and refluxed until the reaction mixture became clear. After the reaction was completed by TLC (7:3/PE:EtOAc; $R_f$~0.4), the reaction mixture was cooled to room temperature and the organic layer was separated. The aq. layer was again extracted with DCM (1×100 mL) and the combined organic layer was washed with water, brine solution. Dried over sodium sulfate and concentrated. The residue was purified by column chromatography over silica gel (60-120 mesh) eluting with DCM as an eluent to afford 2-(3,4-dimethoxyphenyl)-5,7-dihydroxy-6-methoxy-4H-chromen-4-one (precursor compound 10) as a yellow solid (yield: 7.0 g; 66%).

Figure 12:
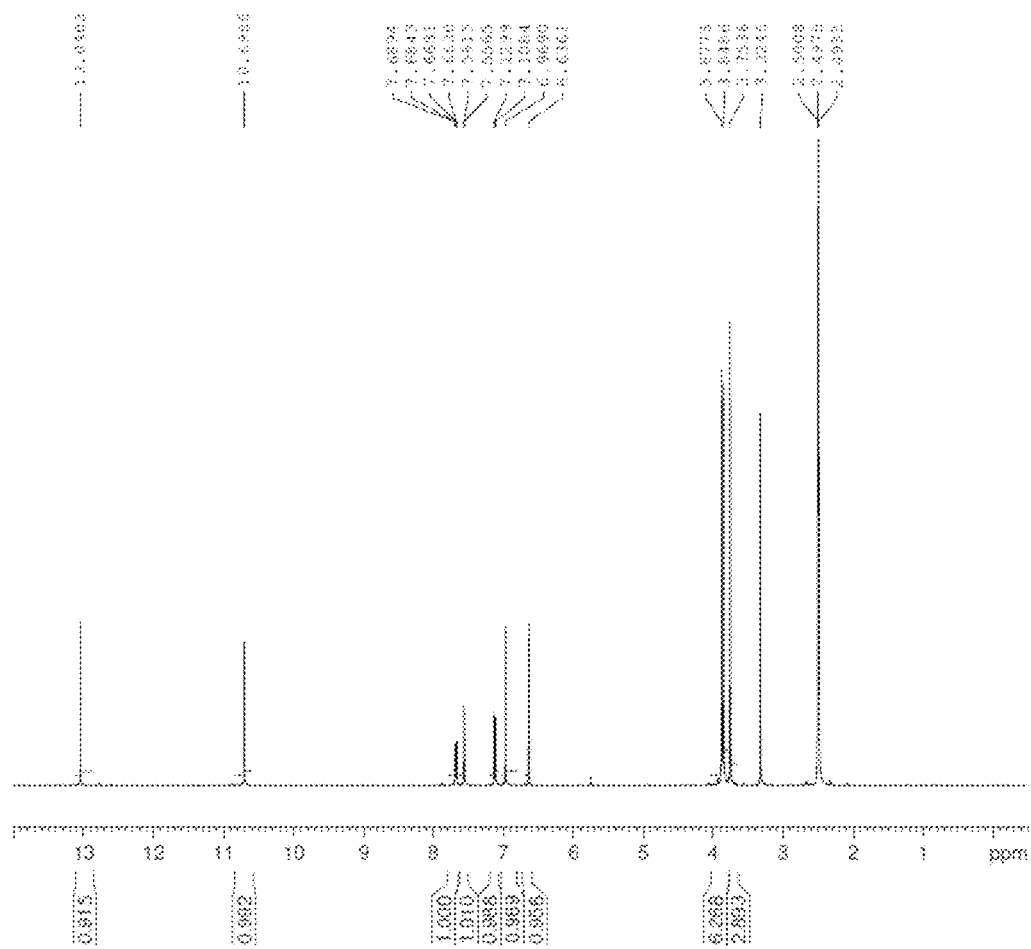
FIG. 12 shows the results of LCMS-NMR analysis of 2-(3,4-dimethoxyphenyl)-5,7-dihydroxy-6-methoxy-4H-chromen-4-one produced in a process of synthesizing a compound of the present invention according to one example of the present invention.

The obtained 2-(3,4-dimethoxyphenyl)-5,7-dihydroxy-6-methoxy-4H-chromen-4-one (precursor compound 10) was analyzed by LCMS-NMR under the following conditions, and the results are shown in FIG. 12.

LCMS: Mass found; (344.9; M+1).
Method: A—0.1% HCOOH in $H_2O$, B: ACN; Flow Rate: 1.5 mL/min; +ve mode.
  Column: Zorbax extended C18 (50×4.6 mm, 5 μm).
  Rt (min): 2.44; Area %—98.32.
  HPLC: 97.64%.
  Mobile Phase: A: 0.1% TFA in WATER, B: ACN; Flow Rate: 1.0 mL/min.
  Column: Atlatis dC-18 (4.6×250) mm; 5u;
  Rt (min): 12.68; Area %—97.64.
  $^1$H-NMR (400 MHz, DMSO-$d_6$): δ 13.05 (s, 1H), 10.73 (s, 1H), 7.68-7.71 (m, 1H), 7.58 (d, J=2.04 Hz, 1H), 7.14 (d, J=8.64 Hz, 1H), 6.99 (s, 1H), 6.65 (s, 1H), 3.89 (s, 3H), 3.86 (s, 3H), 3.76 (s, 3H).
  $^{13}$C-NMR (100 MHz, DMSO-d6): δ 182.6, 163.8, 157.8, 153.1, 152.8, 152.5, 149.4, 131.8, 123.4, 120.4, 112.1, 109.9, 104.5, 103.8, 94.8, 60.4, 56.3, 56.2.

1-10: Synthesis of 7-(2-bromoethoxy)-2-(3,4-dimethoxyphenyl)-5-hydroxy-6-methoxy-4H-chromen-4-one (Precursor Compound 11) (Step-10)

This step is a step of performing step-10 shown in FIG. 3, and the detailed description thereof is as follows.

To a stirred mixture of 2-(3,4-dimethoxyphenyl)-5,7-dihydroxy-6-methoxy-4H-chromen-4-one (precursor compound 10) (10 g, 29 mmol, 1 equiv.) and potassium carbonate (12.04 g, 87.1 mmol, 3.0 equiv.) in THF (400 mL, 40 vol.) were added 1,2-dibromo ethane (27.28 g, 145.2 mol, 5 equiv.) and TBAI (1.05 g, 0.0029 mol, 0.1 equiv.) and the resulting mixture was refluxed at 60° C. for 16 h. After confirming the completion of reaction by TLC analysis, THF was removed under reduced pressure to afford a solid. The crude product was washed with excess of THF and methanol to obtain 7-(2-bromoethoxy)-2-(3,4-dimethoxyphenyl)-5-hydroxy-6-methoxy-4H-chromen-4-one (precursor compound 11) as a solid (yield: 8 g; 61%) The product was used for the next step without any further purification.

Figure 13:
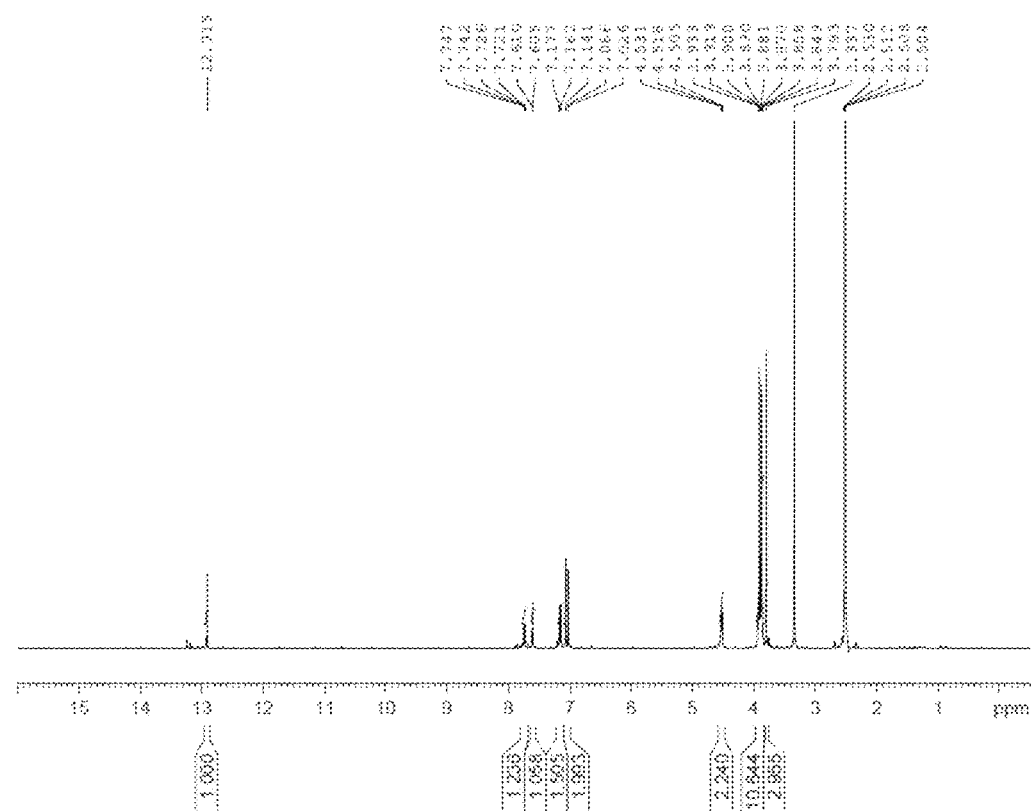
FIG. 13 shows the results of LCMS-NMR analysis of 7-(2-bromoethoxy)-2-(3,4-dimethoxyphenyl-5-hydroxy-6-methoxy-4H-chromen-4-one produced in a process of synthesizing a compound of the present invention according to one example of the present invention.

The obtained 7-(2-bromoethoxy)-2-(3,4-dimethoxyphenyl)-5-hydroxy-6-methoxy-4H-chromen-4-one (precursor compound 11) was analyzed by LCMS-NMR under the following conditions, and the results are shown in FIG. 13.

LCMS: Mass found; (451.0; M+1).

Mobile phase: A: 0.1% HCOOH in H$_2$O, B: ACN; Flow Rate: 1.5 mL/min; +ve mode.
Column: Atlantis dC18 (50×4.6 mm, 5 μm).
Rt (min): 3.14; Area %—80.41.
$^1$H-NMR (400 MHz, DMSO-d$_6$): δ 12.91 (s, 1H), 7.73 (dd, J=5.6, 2.0 Hz, 1H), 7.60 (d, J=2.0 Hz, 1H), 7.15 (d, J=8.4 Hz, 1H), 7.06 (s, 1H), 7.02 (s, 1H), 4.51 (t, J=5.2 Hz, 2H), 3.91 (s, 3H), 3.85 (s, 3H), 3.79 (s, 3H).

1-11: Synthesis of 4-(2-((2-(3,4-dimethoxyphenyl)-5-hydroxy-6-methoxy-4-oxo-4H-chromen-7-yl)oxy) ethyl) piperazin-2-one (Compound 1) (Step-11)

Figure 14:
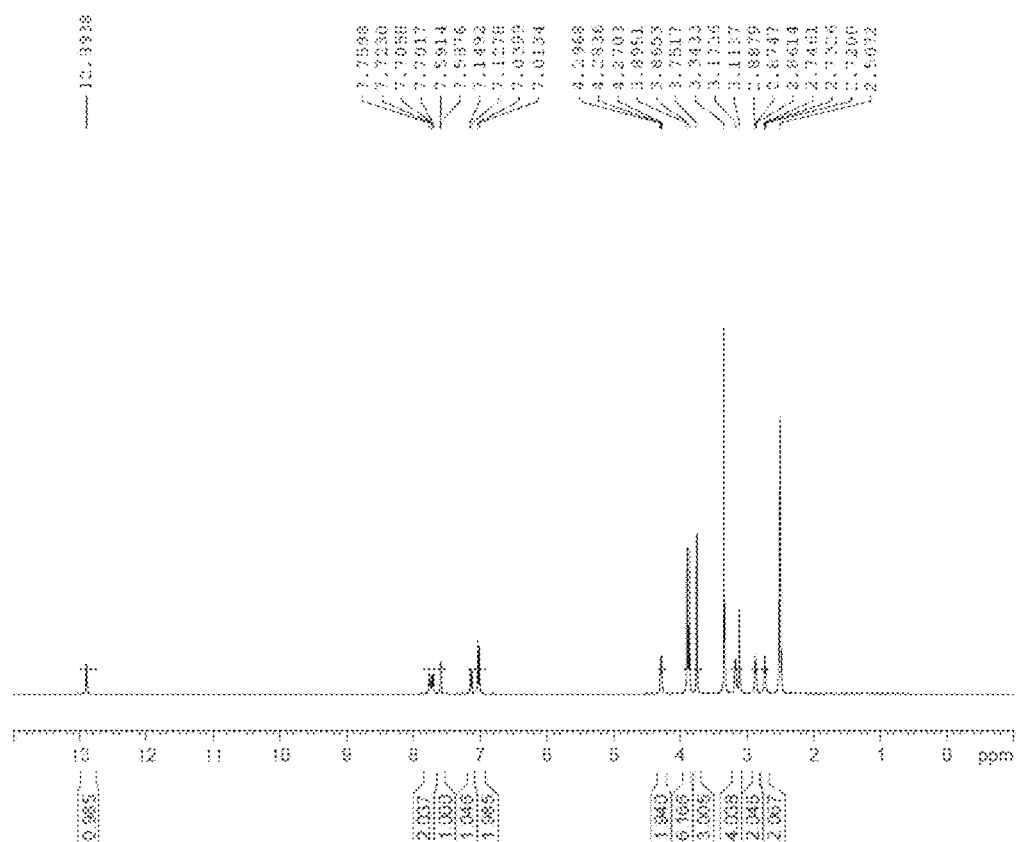
FIG. 14 shows the results of LCMS-NMR analysis of 4-(2-((2-(3,4-dimethoxyphenyl)-5-hydroxy-6-methoxy-4-oxo-4H-chromen-7-yl)oxy)ethyl)piperazin-2-one (a compound of Formula 2) produced in a process of synthesizing a compound of the present invention according to one example of the present invention.

This step is a step of performing step-11 shown in FIG. 3, and the detailed description thereof is as follows.
A solution of 7-(2-bromoethoxy)-3-(3,4-dimethoxyphenyl)-5-hydroxy-6-methoxy-4H-chromen-4-one (precursor compound 11) (8 g, 17.7 mmol, 1.0 equiv.) and piperazine-2-one (5.33 g, 53.3 mmol, 3.0 equiv.) in acetonitrile (80 mL) was refluxed under nitrogen atmosphere for 12 h. After confirming the completion of the reaction by TLC, acetonitrile was removed under reduced pressure. The resultant gum was triturated with DCM and pet-ether to get a solid, which was washed subsequently with methanol, DCM and THF and dried well to afford 4-(2-((2-(3,4-dimethoxyphenyl)-5-hydroxy-6-methoxy-4-oxo-4H-chromen-7-yl)oxy) ethyl)piperazin-2-one (compound 1; Formula 2) (yield: 3.2 g; 41%).
The obtained 4-(2-((2-(3,4-dimethoxyphenyl)-5-hydroxy-6-methoxy-4-oxo-4H-chromen-7-yl)oxy)ethyl)piperazin-2-one (compound 1) was analyzed by LCMS-NMR under the following conditions, and the results are shown in FIG. 14.
LCMS: Mass found (471.2; M+1).
Mobile Phase: A: 0.1% Formic Acid in H$_2$O; B: CAN.
Column: Atlantis dC18 (50×4.6 mm, 5 μm).
Rt (min): 1.515; Area %—95.488.
HPLC: 97.03%.
Mobile Phase: A: 0.1% TFA in H$_2$O; B: Acetonitrile.
Column: Atlantis dC18 (50×4.6 mm, 5 μm).
Rt (min): 9.74; Area %—97.03.
$^1$H NMR: (400 MHz, DMSO-d$_6$): δ 12.89 (s, 1H), 7.75 (br s, 1H), 7.70 (dd, J=8.0, 1.6 Hz, 1H), 7.58 (s, 1H), 7.13 (d, J=8.5 Hz, 1H), 7.02 (d, J=10.4 Hz, 2H), 4.28 (t, J=5.2 Hz, 2H), 3.89 (s, 3H), 3.86 (s, 3H), 3.75 (s, 3H), 3.17 (br s, 2H), 3.11 (s, 2H), 2.87 (t, J=5.2 Hz, 2H), 2.73 (t, J=5.2 Hz, 2H).
$^{13}$C-NMR (100 MHz, CDCl$_3$): 182.4, 169.2, 163.9, 157.5, 153.1, 152.9, 152.2, 149.1, 132.7, 123.4, 119.9, 111.0, 108.6, 106.1, 104.1, 91.4, 67.1, 60.7, 57.0, 56.0, 55.9, 55.5, 49.4, 41.1.

Figure 15:
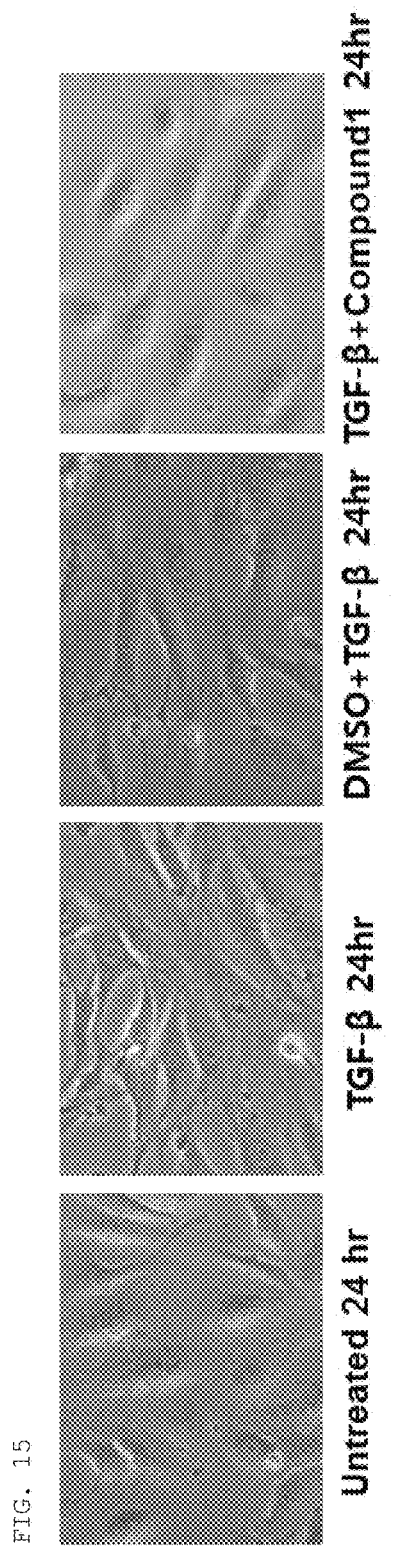
FIG. 15 shows the inhibitory effect of a compound of the present invention against fibrosis of ONGHEPA1 cells which are mesenchymal stem cells (MSCs) derived from hepatic stellate cells (HSCs).
Figure 16:
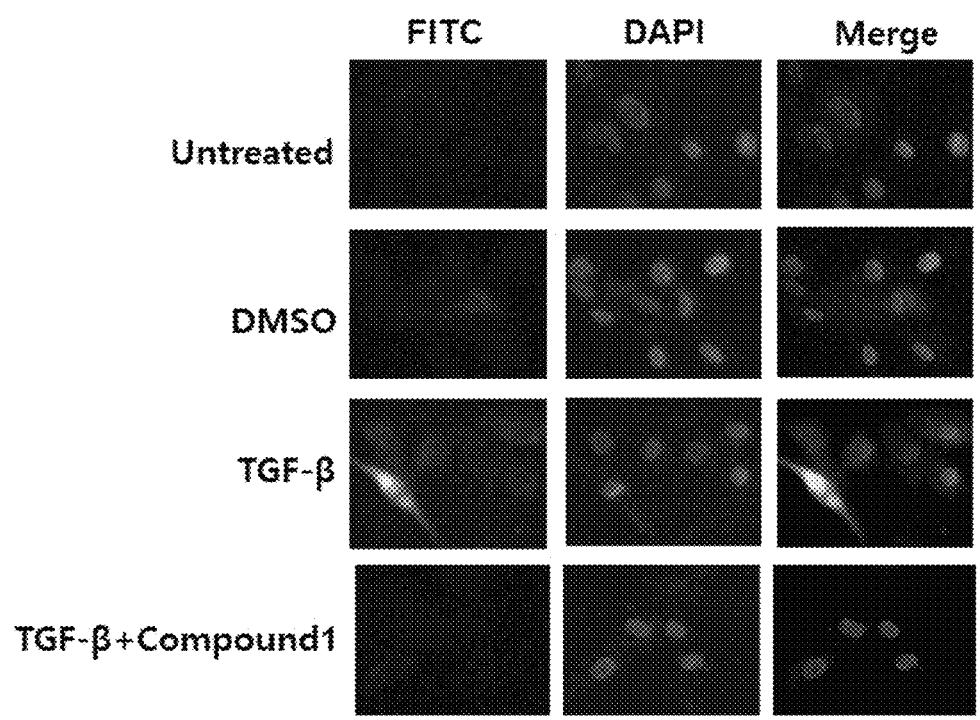
FIG. 16 shows the inhibitory effect of a compound of the present invention against expression of alpha-smooth muscle actin (α-SMA) which is a representative marker of EMT (epithelial-mesenchymal transition) in fibrosis of ONGHEPA1 cells.

Experimental Example 1: Examination of the Effect of Compound of the Present Invention Against Fibrosis 1-1: Experiment on Effect Using Mesenchymal Stem Cells In order to examine the effect of a compound of the present invention against fibrosis, ONGHEPA1 cells (KCTC13086BP), which are mesenchymal stem cells (MSCs) derived from rat hepatic stellate cells (HSCs) and capable of proliferating indefinitely, were first used. Fibrosis of the ONGHEPA1 cells can be induced by a simple method of treating the cells with TGF-β (transforming growth factor beta) or PDGF (platelet-derived growth factor).
The ONGHEPA1 cells were seeded into medium, cultured for 24 hours, and then treated with TGF-β (5 ng/ml) to induce cell fibrosis. Alternatively, the cells were co-treated with TGF-β and the compound of the present invention (50 μM in DMSO) and cultured for 24 hours. Next, the degree of fibrosis of the cells, that is, the degree of differentiation into myofibroblasts, was examined with a phase contrast microscope (200×).
In this regard, the detailed experimental method followed the paper of Kim et al. (Han-Soo Kim, Jun-Hwan Kim, Ji Yong Lee, Young-Min Yoon, Ik-Hwan Kim, Ho-Sup Yoon, Byung-Soo Youn. Small molecule-mediated reprogramming of epithelial-mesenchymal transition thereby blocking fibrosis. bioRxiv preprint first posted online Feb. 16, 2017; doi: http://dx.doi.org/10.1101/106591).
As a result, as shown in FIG. 15, the control group treated with TGF-β differentiated into elongated myofibroblasts, and thus showed a typical fibrosis symptom, whereas the test group treated with TGF-β plus the compound of the present invention showed no fibrosis symptom such that it did not differ from the normal control group.
In addition, in order to examine whether the above-described effect would be attributable to the effect against epithelial-mesenchymal transition (EMT) (hereinafter referred to as "EMT"), the expression of α-SMA (alpha-smooth muscle actin), which is a representative marker of EMT, in the cells of each test group, was examined by immunofluorescent staining and nuclear staining (DAPI staining).
As a result, as shown in FIG. 16, the expression of α-SMA in the control group treated with TGF-β was significantly high, whereas the expression of α-SMA in the test group treated with TGF-β plus the compound of the present invention was inhibited such that it did not differ from that in the normal control group.
These results support that the compound of the present invention strongly inhibits the differentiation of cells into myofibroblasts by affecting the EMT of the cells, and thus can effectively prevent or treat fibrosis, particularly fibrosis or non-alcoholic steatohepatitis (NASH) which occurs in the liver.

Figure 17:
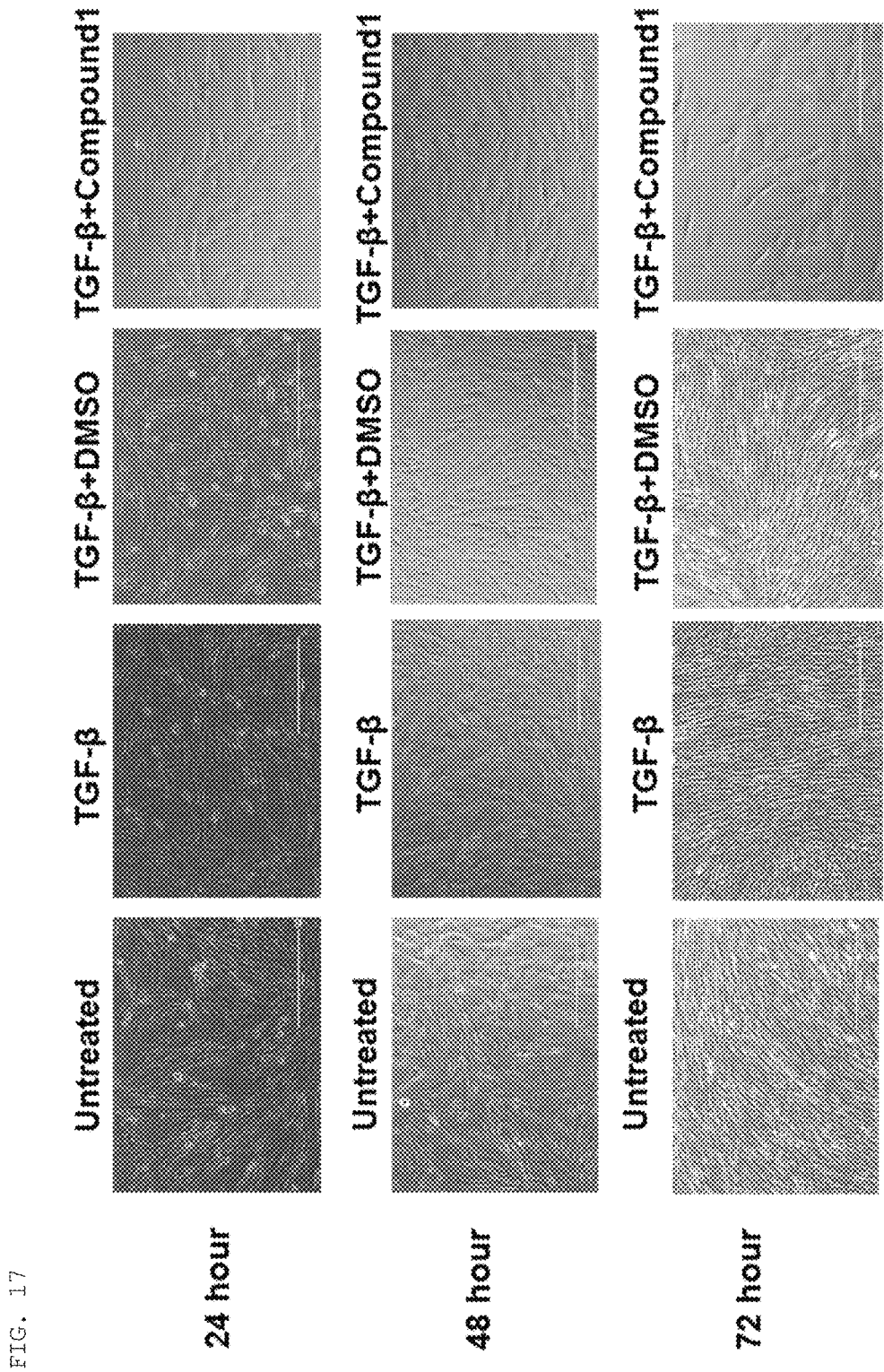
FIG. 17 shows the inhibitory effect of a compound of the present invention against fibrosis of diseased human lung fibroblasts (DHLFs) isolated from lung fibrosis patients.

1-2: Experiment on Effect Using Fibroblasts Isolated from Lung Fibrosis Patients Diseased human lung fibroblasts (DHLF) (Lonza, Swiss) isolated from lung fibrosis patients were seeded into medium, cultured for 24 hours, and then treated with TGF-β (5 ng/ml) to induce fibrosis. Alternatively, the fibroblasts were co-treated with TGF-β and the compound of the present invention (50 μM in DMSO) and cultured for 24, 48 or 72 hours. Next, the degree of differentiation into myofibroblasts was examined with a phase contrast microscope (200×).
As a result, as shown in FIG. 17, the untreated group and the control group treated with TGF-β differentiated into elongated myofibroblasts, and thus showed a typical fibrosis symptom, whereas the test group treated with TGF-β plus the compound of the present invention showed little or no fibrosis symptom, and the growth of the cells was also inhibited.
These results support that the compound of the present invention strongly inhibits the growth and fibrosis of fibroblasts already programmed to become fibrous and restores the fibroblasts to normal cells, indicating that it can effectively prevent or treat fibrosis, particularly fibrosis such as idiopathic pulmonary fibrosis which occurs in lungs.

1-3: Experiment on Effect Using Lung Adenocarcinoma Cell Line

The A549 cell line, which is a lung adenocarcinoma cell line used as a lung EMT-related study model, was seeded into medium, cultured for 24 hours, and then treated with TGF-β (5 ng/ml). Alternatively, the A549 cell line was co-treated with TGF-β and the compound of the present invention (25 or 50 μM in DMSO) and cultured for 24 or 48 hours. Next, the cells were examined with a phase contrast microscope (200×).

Figure 18:
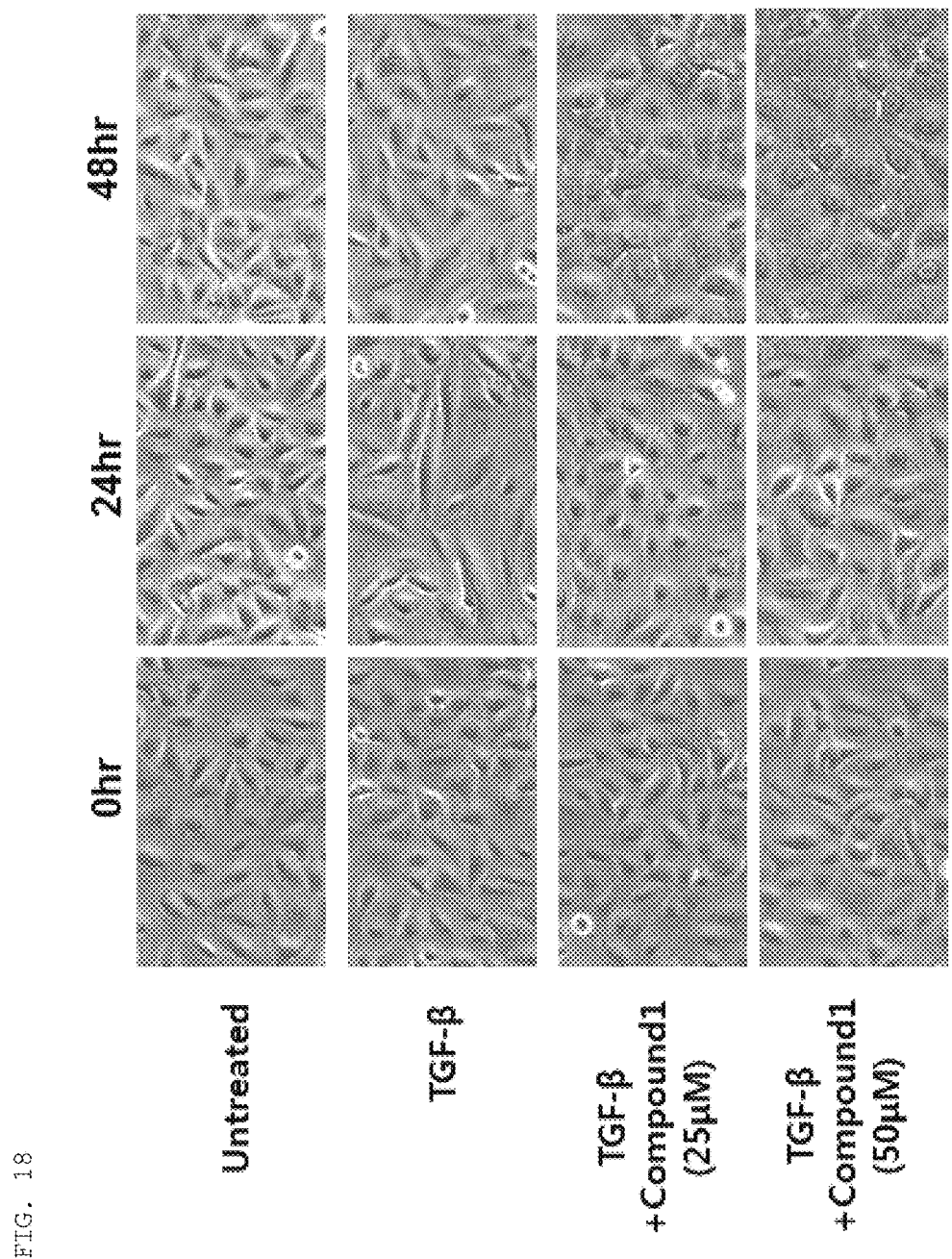
FIG. 18 shows the inhibitory effect of a compound of the present invention against fibrosis of the A549 cell line which is a human lung adenocarcinoma cell line.

As a result, as shown in FIG. 18, the control group treated with TGF-β differentiated into myofibroblasts, whereas myofibroblast differentiation of the test group treated with TGF-β plus the compound of the present invention was inhibited.

In addition, in order to examine whether the effect as described above would be attributable to the effect against EMT, the expression patterns of Snail and Vimentin, which are representative markers of EMT, in the cells of each test group, were analyzed by real-time PCR.

Figure 19:
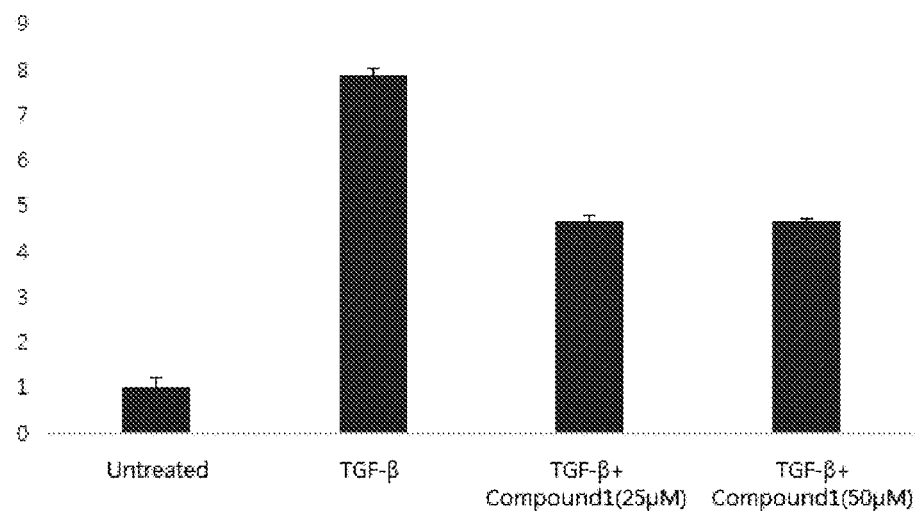
FIG. 19 shows the inhibitory effect of a compound of the present invention against expression of Snail and Vimentin which are representative markers of EMT in the A549 cell line.
Figure 19:
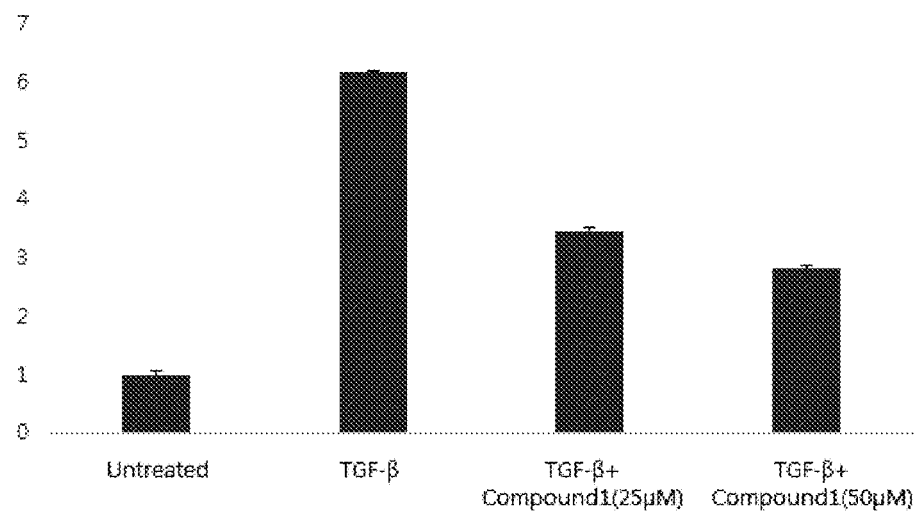

As a result, as shown in FIG. 19, the expression of these markers in the control group treated with TGF-β significantly increased, whereas the expression of these markers in the test group treated with TGF-β plus the compound of the present invention was significantly inhibited.

These results support that the compound of the present invention strongly inhibits the differentiation of cells into myofibroblasts by affecting the EMT of the cells, and thus can effectively prevent or treat fibrosis, particularly fibrosis such as idiopathic pulmonary fibrosis which occurs in lungs.

Experimental Example 2: Examination of Pharmacokinetics of Compound of the Present Invention

2-1: Metabolic Stability

The compound of the present invention was incubated with rat liver microsomes and NADPH, and then the rate of elimination of the compound was measured, thereby determining the intrinsic clearance value (CLint value) of the compound. As controls, verapamil and atenolol were used.

Figure 20:
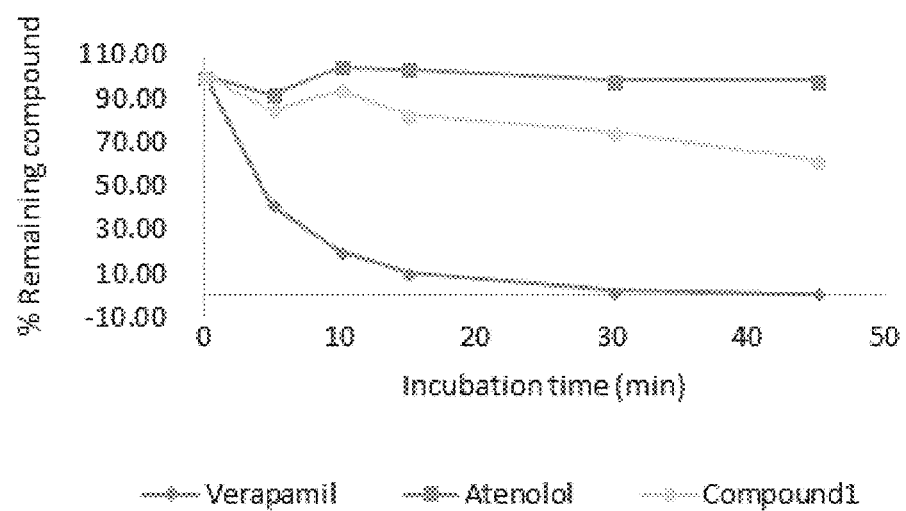
FIG. 20 shows the results of evaluating the metabolic stability of a compound of the present invention for liver microsomes.

As a result, it was shown that the compound of the present invention was metabolically stable such that it could be comparable with atenolol (see Table 1 below and FIG. 20).

TABLE 1

| Compound name | Rat liver microsomes | | |
|---|---|---|---|
| | t½ (min) | CL int (μl/min/ mg protein) | Clearance value |
| Compound 1 | 71.43 | 19.40 | Moderate |
| Verapamil | 6.37 | 217.68 | High |
| Atenolol | 9415.85 | 0.15 | Low |

2-2: Solubility in Buffer

The compound of the present invention was added to phosphate buffer (pH 7.4) at a concentration of 1 mg/ml and stirred. After 16 hours, the sample was filtered through a filter, and the supernatant was analyzed by HPLC-UV, thereby determining the content of compound dissolved. As controls, caffeine and diethyl stilbesterol were used.

As a result, it was shown that the solubility of the compound of the present invention in the buffer was lower than that of caffeine, but higher than that of diethyl stilbesterol (see Table 2 below).

TABLE 2

| Compound name | Solubility (μg/ml) |
|---|---|
| Caffeine | 972.68 |
| Diethyl stilbesterol | 4.50 |
| Compound 1 | 9.59 |

2-3: Whether to Inhibit CYP450

Whether the compound of the present invention inhibits CYP3A4, CYP2D6 and CYP2C9 was examined. As controls, ketoconazole, quinidine and sulfaphenazole were used.

As a result, it was shown that the compound of the present invention had slight inhibitory activity against CYP2C9, but this inhibitory activity was lower than that of the control sulfaphenazole, and the compound of the present invention had little or very low inhibitory activity against CYP3A4 and CYP2D6 (see Table 3 below).

TABLE 3

| Compound name | 3A4-midazolam IC50 (μM) | 3A4-testosterone IC50 (μM) | 2D6 IC50 (μM) | 2C9 IC50 (μM) |
|---|---|---|---|---|
| Compound 1 | >50 | 49.72 | >50 | 5.54 |
| Ketoconazole | 0.027 | 0.023 | na | na |
| Quinidine | na | na | 0.047 | na |
| Sulfaphenazole | na | na | na | 0.40 |

*na: not activity

2-4: Pharmacokinetics after Oral Administration

To examine the pharmacokinetics of the compound after oral administration, rat models were used.

Male SD rats (weighed 250 to 300 g) were divided into several groups, each consisting of 3 rats, and the compound of the present invention was orally administered thereto at 200 mpk, after which the amount of the compound present in the plasma was measured with the passage of time. For oral administration, the compound was formulated with 0.5% CMC and about 1% Tween-80 [Tween80: 0.5% CMC aqueous solution=1:99 (v/v)] and used.

Figure 21:
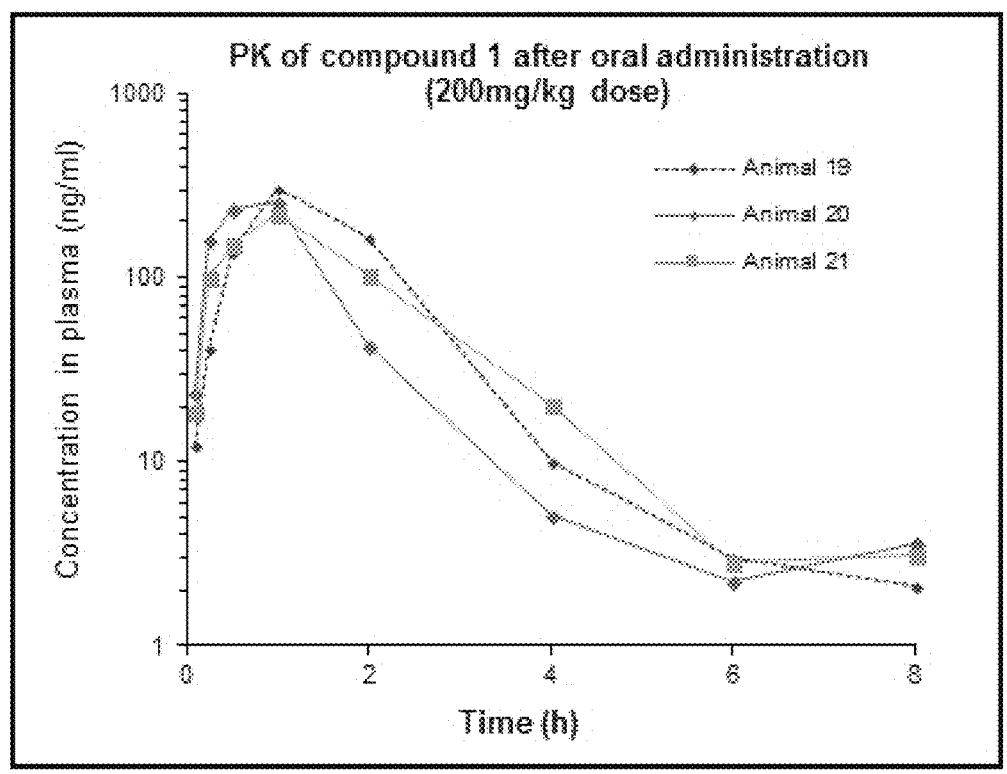
FIG. 21 shows the results of evaluating the pharmacokinetics of a compound of the present invention after oral administration.
Figure 21:
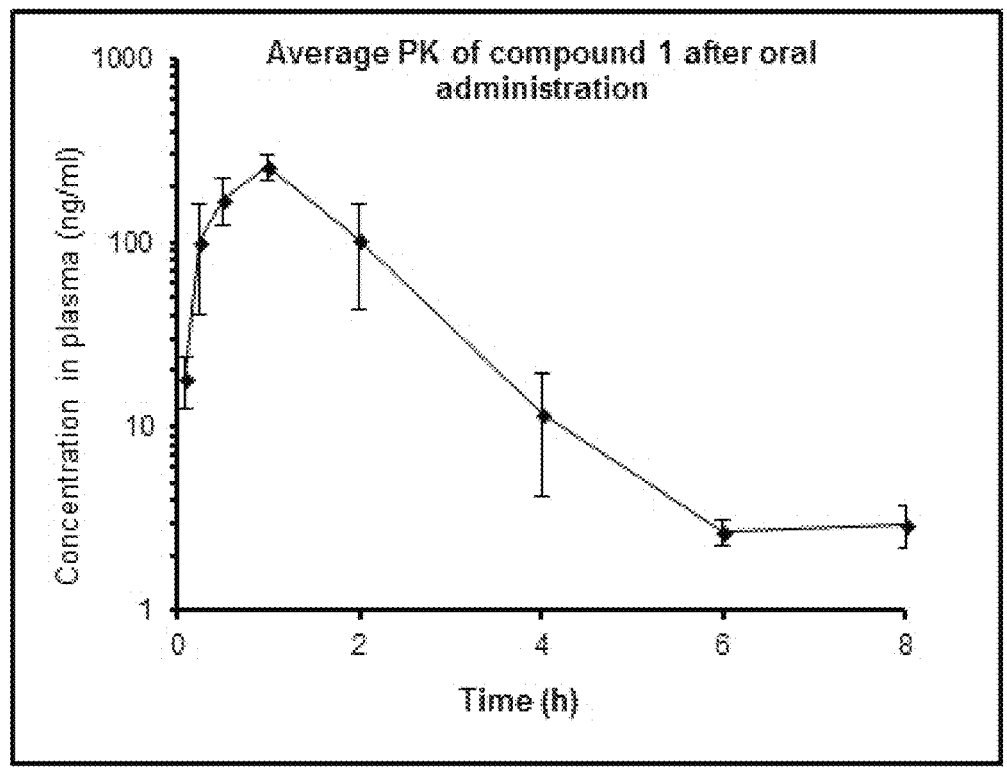

As a result, it was shown that the compound of the present invention could be absorbed rapidly in vivo after oral administration (see Table 4 below and FIG. 21).

TABLE 4

| PK parameters | Compound 1 (200 mpk, po) |
|---|---|
| Cmax (ng/ml) | 260.8 ± 41.4 |
| Tmax (h) | 1 ± 0 |
| AUC (inf) (h * ng/ml) | 426.5 ± 67.7 |
| AUC (0-24) (h * ng/ml) | 420.1 ± 69.3 |
| AUC_%Extrap (obs) | 1.6 ± 0.7 |
| MRT (inf) (h) | 1.7 ± 0.2 |
| t½ (h) | 1.5 ± 0.4 |

* Mean ± SD n = 3 rats/group)

Comparative Experimental Example 1: Examination of the Effect of Comparative Examples Against Fibrosis The effects of the following comparative compounds against fibrosis were examined in the same manner as described in Experimental Example 1-1 above.

Figure 22:
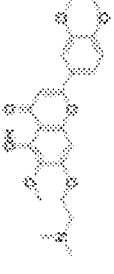
Figure 22:
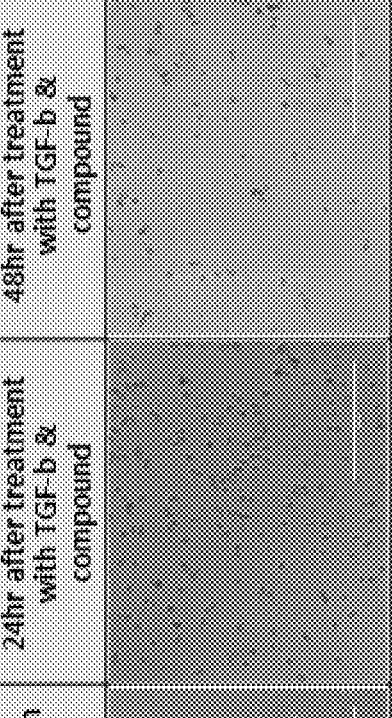
Figure 22:
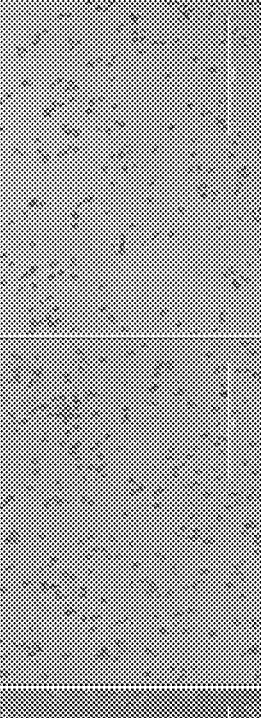
Figure 23:
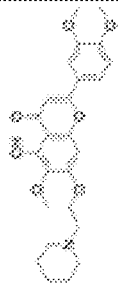
Figure 24:
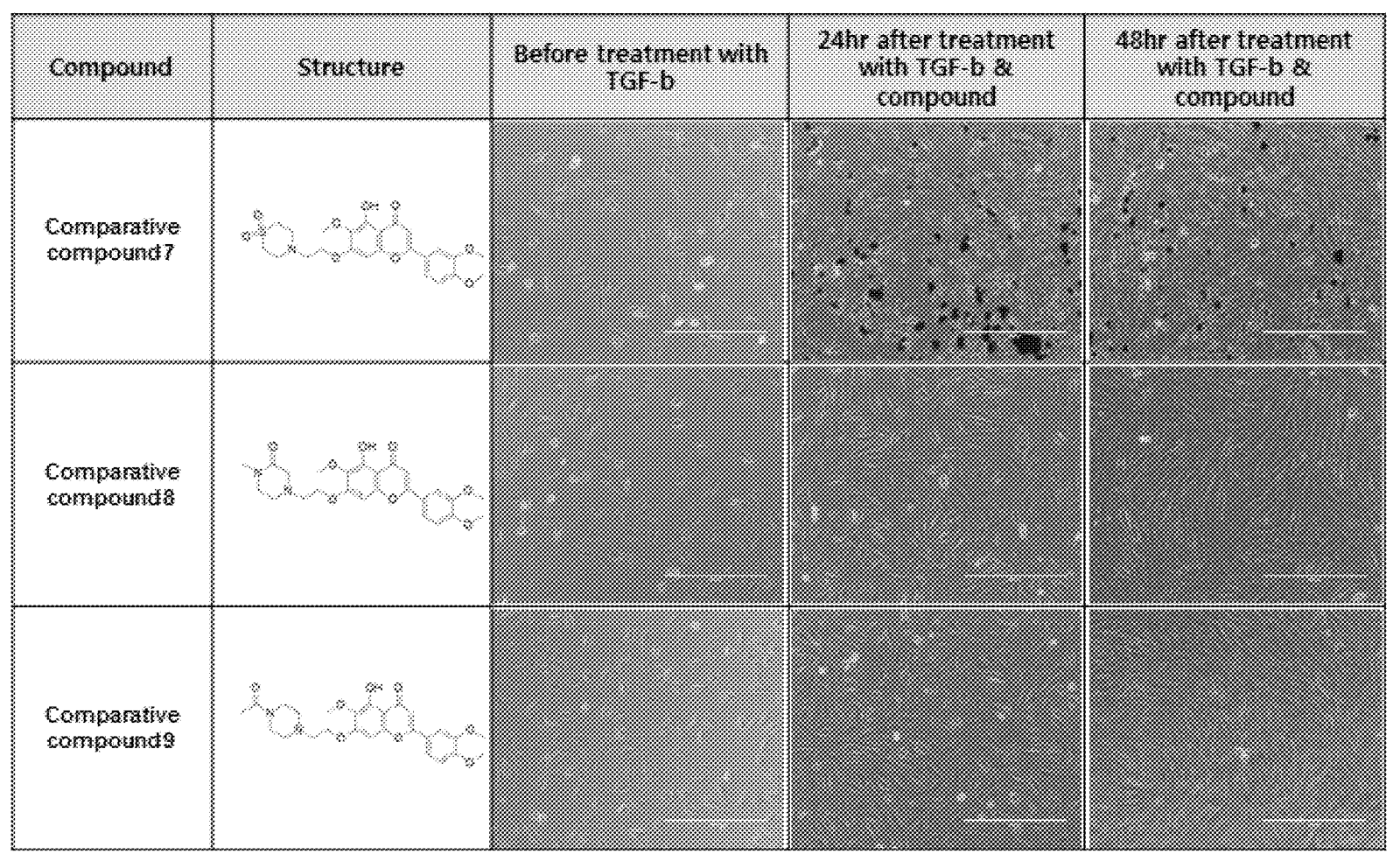

As a result, as shown in FIGS. 22 to 24, unlike the compound of the present invention, the comparative compounds failed to induce cell death by cytotoxicity and to block the progression of cell fibrosis.

Comparative compound 1
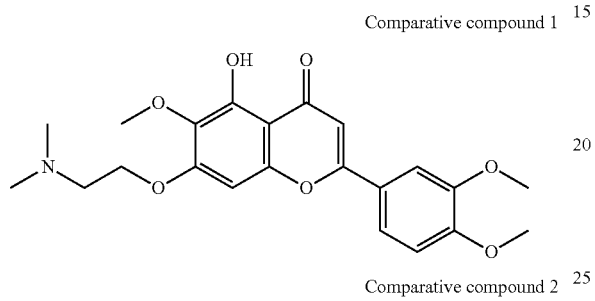

Comparative compound 2
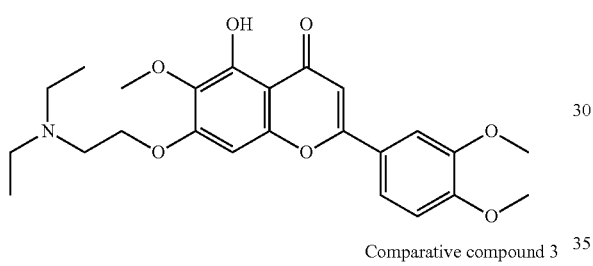

Comparative compound 3
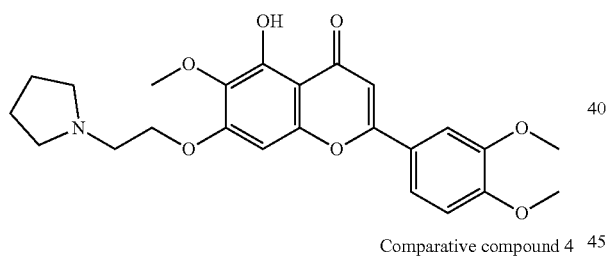

Comparative compound 4
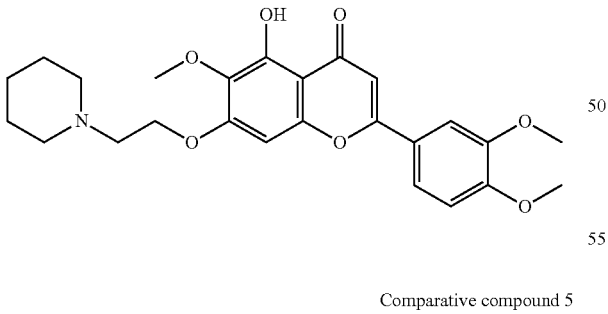

Comparative compound 5
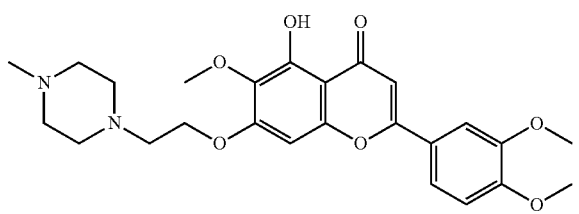

Comparative compound 6
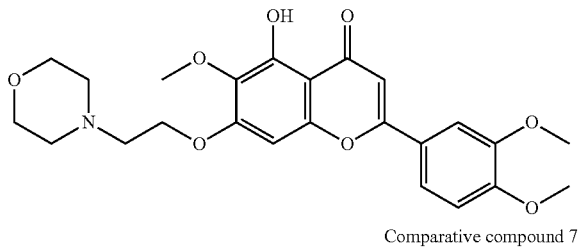

Comparative compound 7
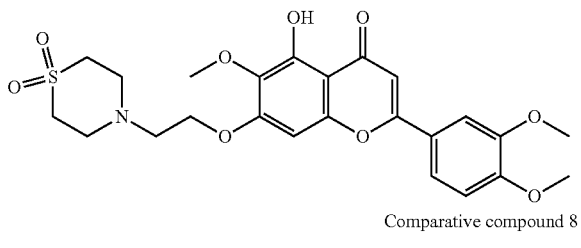

Comparative compound 8
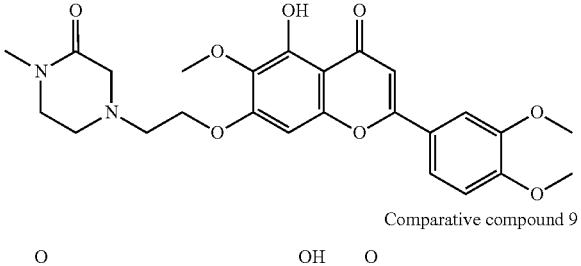

Comparative compound 9
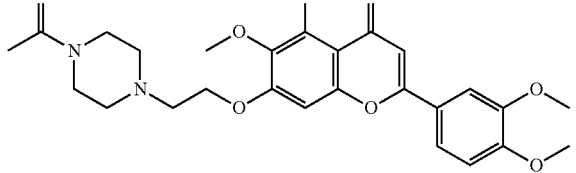

Experimental Example 3: Pharmacokinetics of Formulations

For effective formulation of the compound of the present invention, the pharmacokinetics of various formulations after oral administration were examined according to the same method as described in Experimental Example 2-4 above.

As a result, as shown in Table 5 below, when the compound was formulated using Tween80: 0.5% CMC aqueous solution (1:99 v/v) (Formulation Example 2), the bioavailability of the compound was as low as 1.4%, and when the compound was formulated using NMP:ethanol:PEG200: normal saline (5:10:30:55 v/v) (Formulation Example 4), the bioavailability of the compound was about 3%. On the other hand, it was shown that when the compound was formulated using NMP:PEG400:SOLUTOL HS:water (10:20:20:50 v/v) (Formulation Example 3), the bioavailability of the compound was greatly improved to about 9%, and when the compound was formulated using 30% HPCD aqueous solution (Formulation Example 5), the bioavailability of the compound was also greatly improved to about 7%.

TABLE 5

| PK parameters | Compound 1 (1 mpk, i.v) | Compound 1 (10 mpk, po) | Compound 1 (200 mpk, po) | Compound 1 (10 mpk, po) | Compound 1 (10 mpk, po) | Compound 1 (10 mpk, po) |
|---|---|---|---|---|---|---|
| | Formulation Example 1 | Formulation Example 2 | Formulation Example 2 | Formulation Example 3 | Formulation Example 4 | Formulation Example 5 |
| $C_0$ (ng/ml) | 506.4 ± 129.7 | — | — | — | — | — |
| Cmax (ng/ml) | — | 22.3 ± 8.9 | 260.8 ± 41.4 | 62.2 ± 37.5 | 46.7 ± 8.8 | 393.3 ± 299.3 |
| Tmax (h) | — | 0.4 ± 0.1 | 1 ± 0 | 0.25 ± 0.1 | 0.25 ± 0.0 | 1.3 ± 0.6 |
| $AUC_{(inf)}$ (h*ng/ml) | 149.3 ± 3.0 | — | 426.5 ± 67.7 | 155.2 ± 7.5 | 46.4 ± 14.1 | 1075.9 ± 326.9 |
| $AUC_{(0-t)}$ (h*ng/ml) | 146.6 ± 2.2 | 20.4 ± 6.2 | 420.1 ± 69.3 | 126.2 ± 19.1 | 42.5 ± 16.0 | 1000.5 ± 313.5 |
| AUC_% Extrap (obs) | 1.8 ± 0.5 | — | 1.6 ± 0.7 | — | — | 7.0 ± 5.2 |
| Vd (L/kg) | 3.6 ± 0.25 | — | — | — | — | — |
| CLP (L/hr/kg) | 6.7 ± 0.4 | — | — | — | — | — |
| $MRT_{(inf)}$ (h) | 0.4 ± 0.0 | — | 1.7 ± 0.2 | — | — | 3.2 ± 0.7 |
| $t_{1/2}$ (h) | 0.38 ± 0.03 | — | 1.5 ± 0.4 | — | — | 1.9 ± 0.6 |
| Bioavailability (%) | — | 1.4 | 1.4 | 9 | 3 | 7 |

*Formulation Example 1 - Use of 100% DMSO as i.v. vehicle
*Formulation Example 2 - Use of Tween80: 0.5% CMC aqueous solution (1:99 v/v)
*Formulation Example 3 - Use of NMP: PEG400: SOLUTOL HS: water (10:20:20:50 v/v)
*Formulation Example 4 - NMP: Use of ethanol: PEG200: normal saline (5:10:30:55 v/v)
*Formulation Example 5 - Use of 30% (w/v) HPCD (hydroxypropyl-beta-cyclodextrin) aqueous solution.

Figure 25:
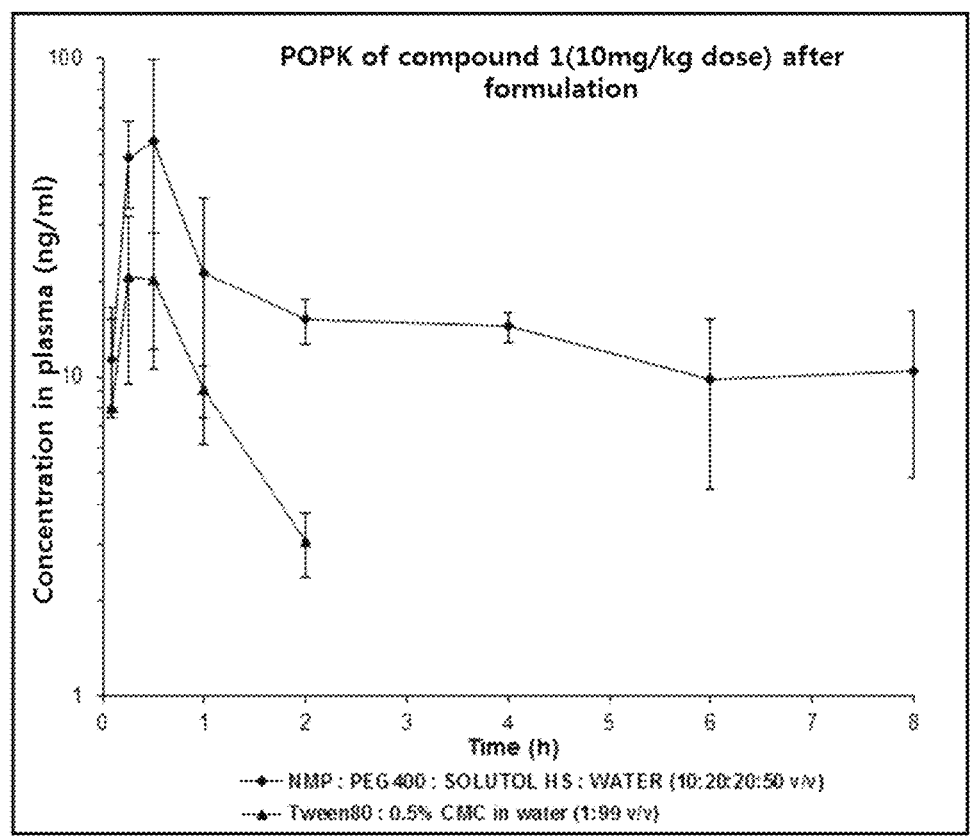
FIG. 25 shows the results of comparing the pharmacokinetics of a compound of the present invention after formulation.

In addition, as shown in FIG. 25, the compound in Formulation Example 2 was absorbed rapidly in vivo after oral administration and was maintained in the plasma for a long period of time without being eliminated, compared to the compound in Formulation Example 3, indicating that it could exhibit a long-lasting effect.

In addition, formulation was attempted by other methods, but in most cases, there was a problem in that the compound was not completely dissolved and the solution became turbid. Due to this problem, these methods were excluded from additional pharmacokinetic studies.

Experimental Example 4: Examination of the Effect of Compound of the Present Invention Against Fibrosis in Animal Models 5-week-old male C57BL/6 mice (weighed 18.2 to 20.5 g) (KOATECH, Korea) were used as experimental animals and divided into several groups, each consisting of 5 animals.

The experimental animals were housed in a housing box having a size of 369 L×156 W×132H (mm) (EU, USA, UK GL compliance) made of a polysulfone material in a SPF (Specific Pathogen Free) and BSL (Bio Safety Level) 2 grade facility. The number of animals in each housing box was 2 to 3 during the period of quarantine and acclimatization and was also 2 to 3 during the experimental period, and the housing conditions were set to a temperature of 22±2° C., a relative humidity of 50.0±15.0%, a ventilation cycle of 10 to 20 times/hr, a light-dark cycle (a photoperiod) of 12 hr/day (07:00 to 19:00), and an illumination intensity of 150 to 300 Lux.

Pulmonary fibrosis was induced by injecting a bleomycin solution directly into the lungs via the trachea according to the intratracheal instillation (IT) method of Kremer, Laxer and Berkman et al. Specifically, C57BL/6J mice were anesthetized through inhalation with 70% $N_2O$ and 30% $O_2$ gas and 1.5% isoflurane, and the skin of the anterior neck thereof was excised and the organs under the muscle thereof were exposed and then carefully excised using ophthalmic surgical scissors. 50 μL of a solution of bleomycin in distilled water was injected directly into the lungs all at once via the excised organ by use of a 1 mL syringe fitted with a 19-gauge injection needle having a blunt tip. Immediately after the injection, the excised skin of the anterior neck was sutured and the mice were allowed to recover from the anesthetic, and then housed in a general housing cage. The administration of bleomycin was performed using a visual instillobot, and bleomycin-HCl 40 μg/50 μL was administered once and a pulmonary fibrosis induction period of 12 days was set.

The compound of the present invention was used after dissolution in 30% HPCD aqueous solution (Formulation Example 5), and the dose for each individual was calculated based on the recent body weight thereof. 12 Days after the administration of bleomycin, the compound of the present invention was administered once a day (5 times a week) for 2 weeks. As a control, pirfenidone which is a therapeutic agent for idiopathic pulmonary fibrosis was administered in the same manner.

Figure 26:
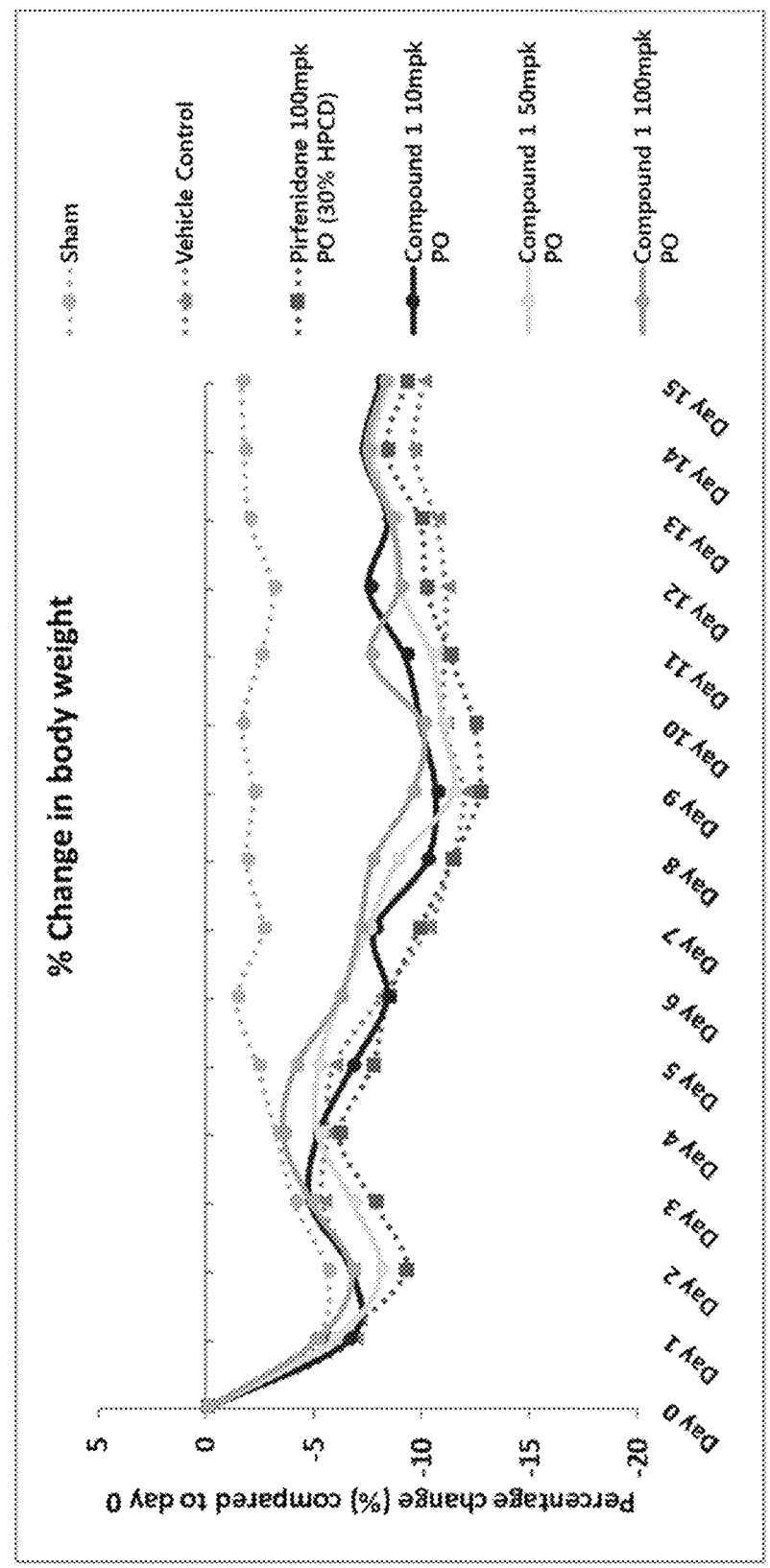
FIG. 26 is a graph showing the change in body weight of fibrotic animal models by administration of a compound of the present invention or a control compound (pirfenidone). Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.

Changes in the body weight for 0-15 days after administration of the compound of the present invention or pirfenidone were examined, and the results are shown in FIG. 26.

Figure 27:
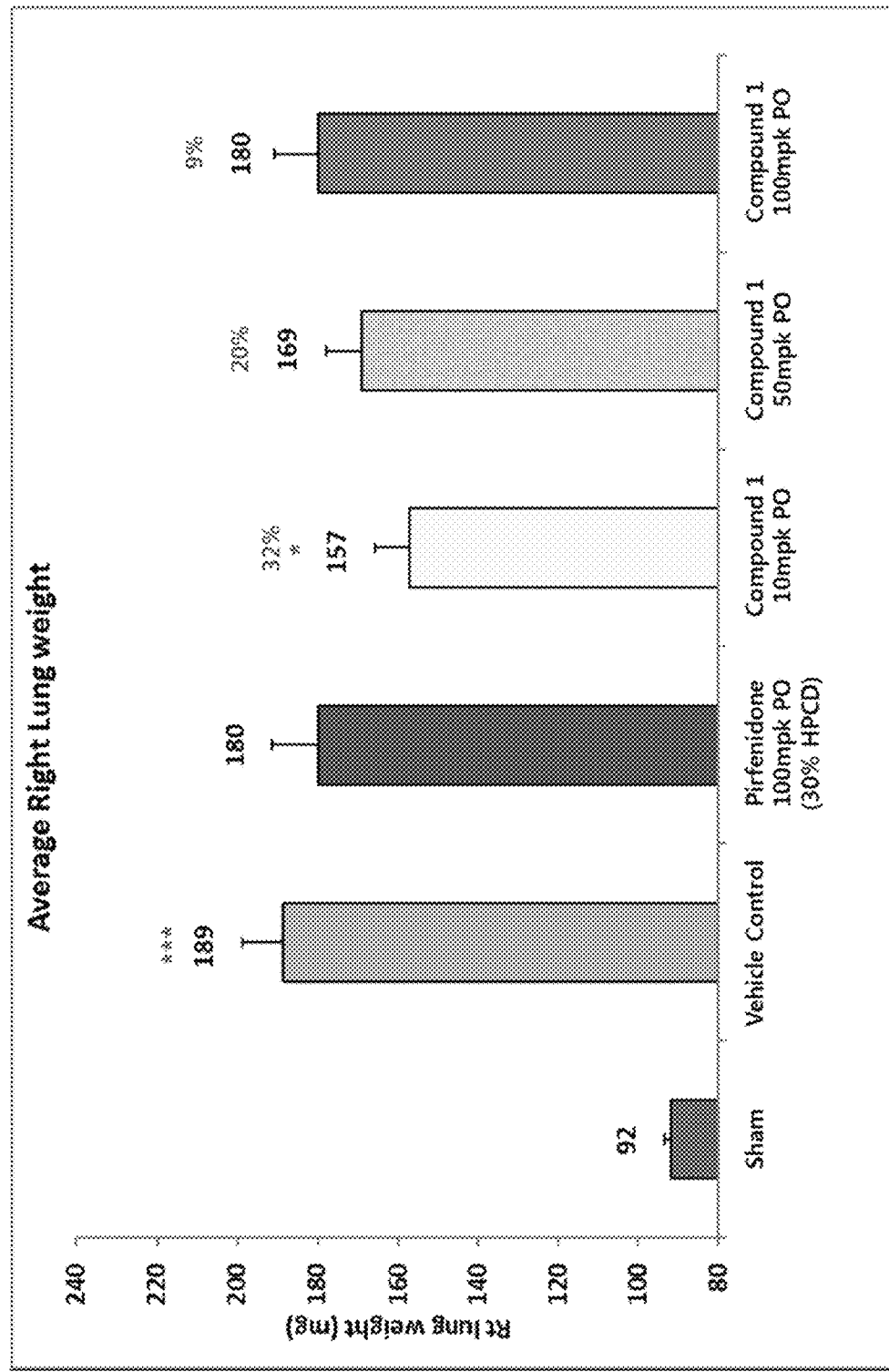
FIG. 27 is a graph showing the change in right lung weight of fibrotic animal models by administration of a compound of the present invention or a control compound (pirfenidone). Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.

On 15 days after administration of the compound, the mice were sacrificed, and then the right lung of each mouse was dissected and the weight thereof was measured. As a result, it was shown that as pulmonary fibrosis was induced by administration of bleomycin, the weight of the right lung increased, and the compound of the present invention significantly inhibited this increase in the right lung weight (see FIG. 27). In particular, it is noted that the inhibitory effect of the compound in the group administered at 10 mpk was the highest compared to that in the group administered at 50 or 100 mpk and was also higher than that in the group administered with pirfenidone 100 mpk.

Figure 28:
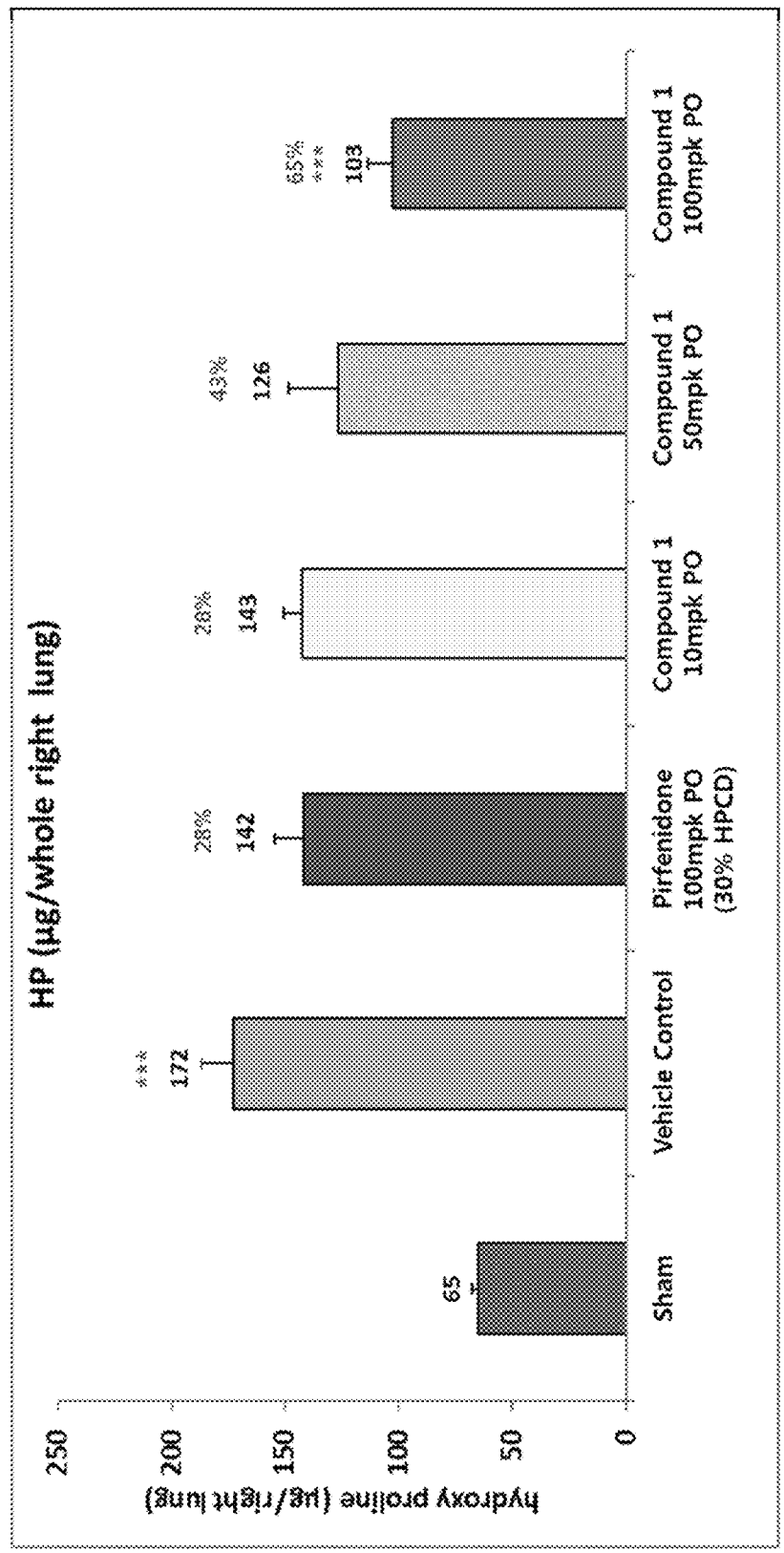
FIG. 28 is a graph showing the change in hydroxyproline amount in right lung of fibrotic animal models by administration of a compound of the present invention or a control compound (pirfenidone). Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.
Figure 29:
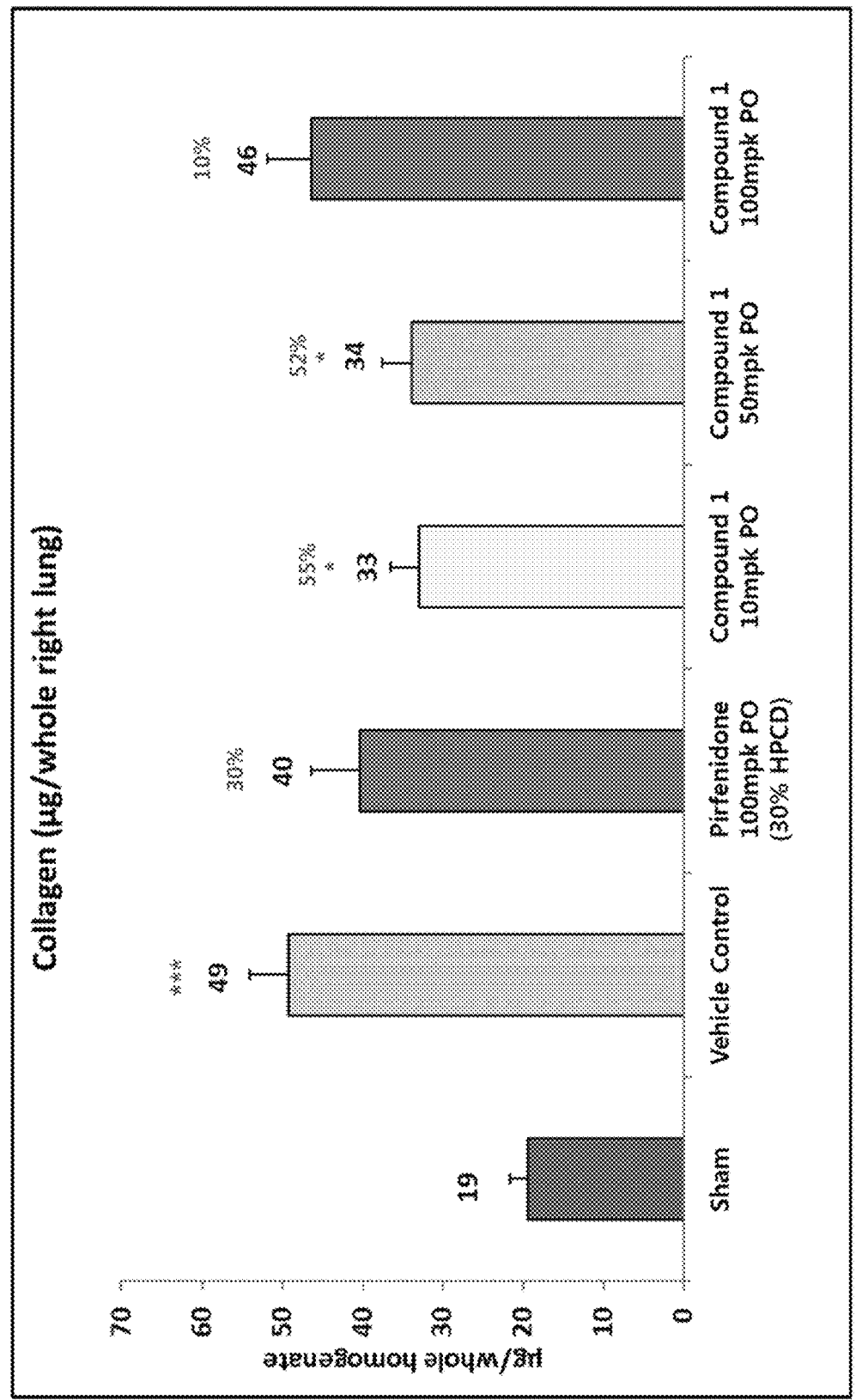
FIG. 29 is a graph showing the change in collagen amount in right lung of fibrotic animal models by administration of a compound of the present invention or a control compound (pirfenidone). Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.

The amounts of hydroxyproline (HP) and collagen in the dissected right lung were measured using a known method. As a result, it was shown that as pulmonary fibrosis was induced by administration of bleomycin, the amounts of hydroxyproline (HP) and collagen in the dissected right lung increased, and the compound of the present invention significantly inhibited this increase (see FIGS. 28 and 29). The results of measurement of hydroxyproline indicated that the inhibitory effect of the compound of the present invention was highest in the group administered at 100 mpk, and the results of measurement of collagen indicated that the inhibitory effect of the compound of the present invention was highest in the group administered at 100 mpk, like the results of measurement of the right lung weight.

Figure 30:
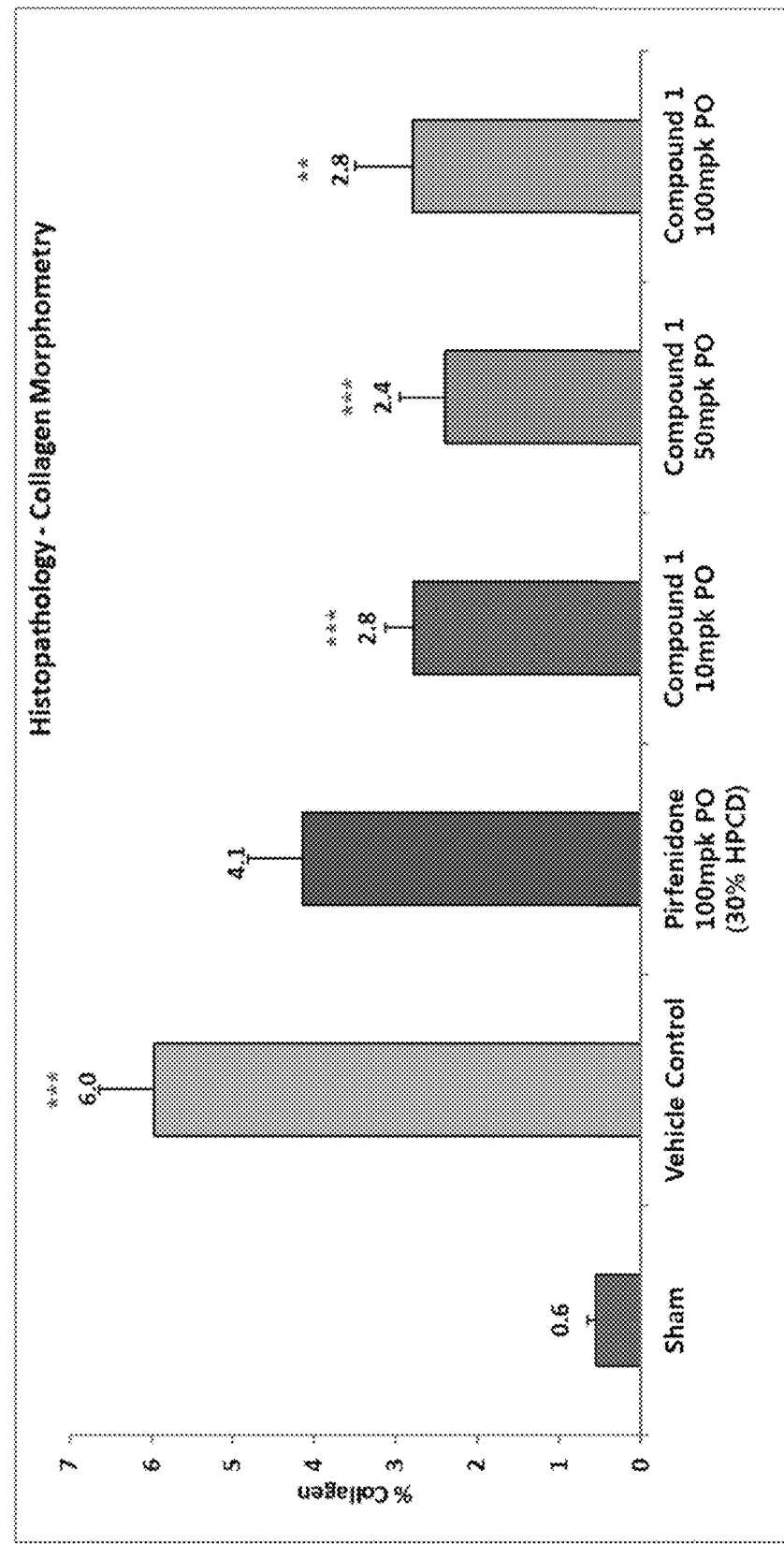
FIG. 30 shows the results of performing histopathology collagen morphometry of the left lung tissues of fibrotic animal models administered with a compound of the present invention or a control compound (pirfenidone). Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.

Histopathology collagen morphometry of the dissected left lung tissue was performed using a known method (calculating the area of collagen in an optical image obtained by Sirius red staining of the lung tissue sample). As a result, it was shown that as pulmonary fibrosis was induced by administration of bleomycin, an increased amount of collagen was observed, and the compound of the present invention significantly inhibited this increase (see Table 6 below and FIG. 30).

Experimental Example 5: Examination of the Effect of Compound of the Present Invention Against Non-Alcoholic Steatohepatitis in Animal Models STAM mice (SMC Laboratories, Inc., Japan), which are non-alcoholic steatohepatitis animal models, were used as experimental animals. These animal models were adminis-

TABLE 6

| Group | Histopathology | Mean Collagen % | SEM Collagen % | Protection Collagen % | T-test P value Collagen % | T-test Significance Collagen % |
|---|---|---|---|---|---|---|
| 1 | Sham | 0.6 | 0.1 | | | |
| 2 | Vehicle control | 6.0 | 0.7 | | 0.0000 | *** |
| 3 | Pirfenidone 100 mpk PO (30% HPCD) | 4.1 | 0.7 | 34 | 0.0653 | NS |
| 4 | Compound 1 10 mpk PO | 2.8 | 0.4 | 59 | 0.0005 | *** |
| 5 | Compound 1 50 mpk PO | 2.4 | 0.6 | 66 | 0.0006 | *** |
| 6 | Compound 1 100 mpk PO | 2.8 | 0.7 | 59 | 0.0041 | ** |

NS: not significant

Figure 31:
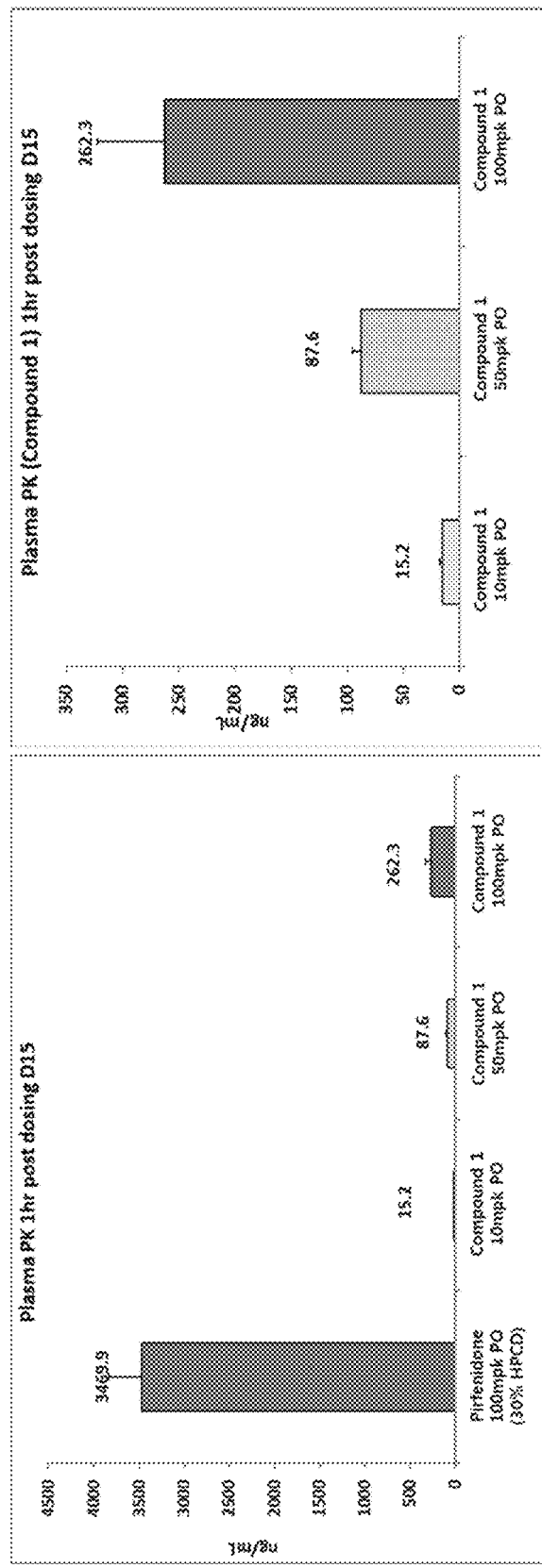
FIG. 31 shows the results of examining the concentration of a compound present in the plasma of fibrotic animal models administered with a compound of the present invention or a control compound (pirfenidone). Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.
Figure 32:
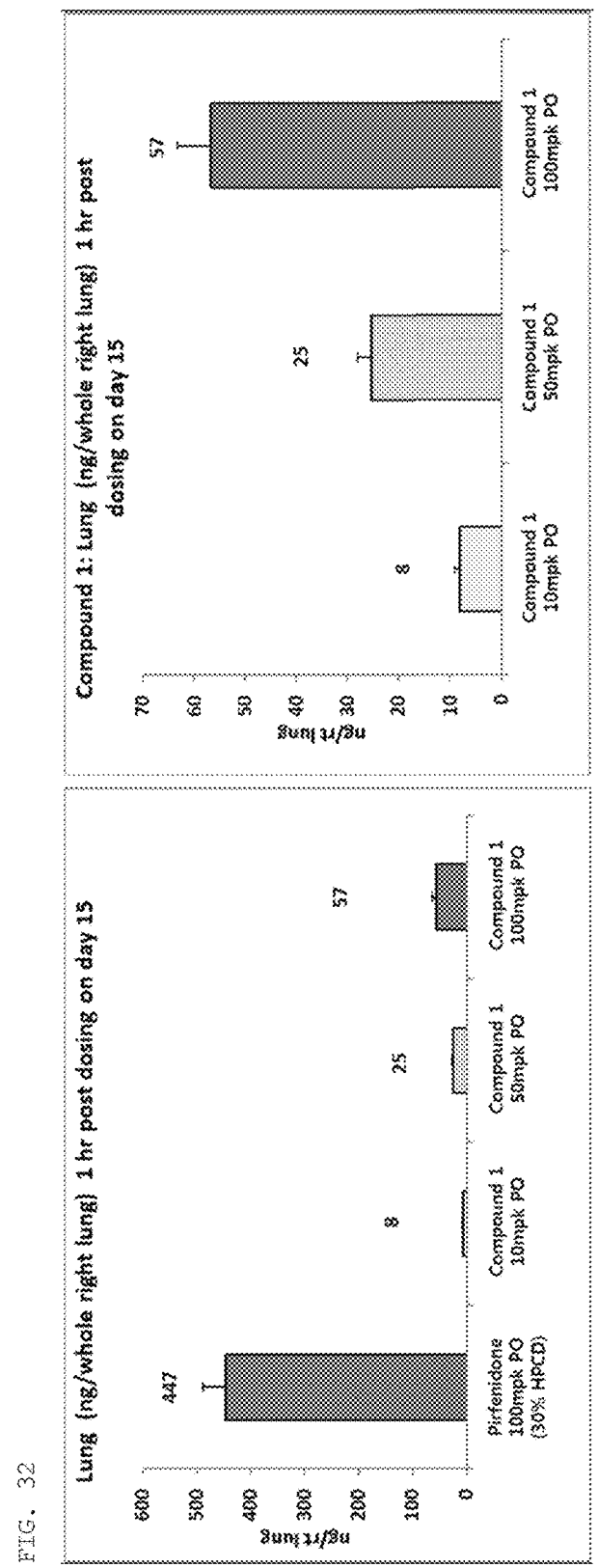
FIG. 32 shows the results of examining the concentration of a compound present in the right lungs of fibrotic animal models administered with a compound of the present invention or a control compound (pirfenidone). Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk.
Figure 33:
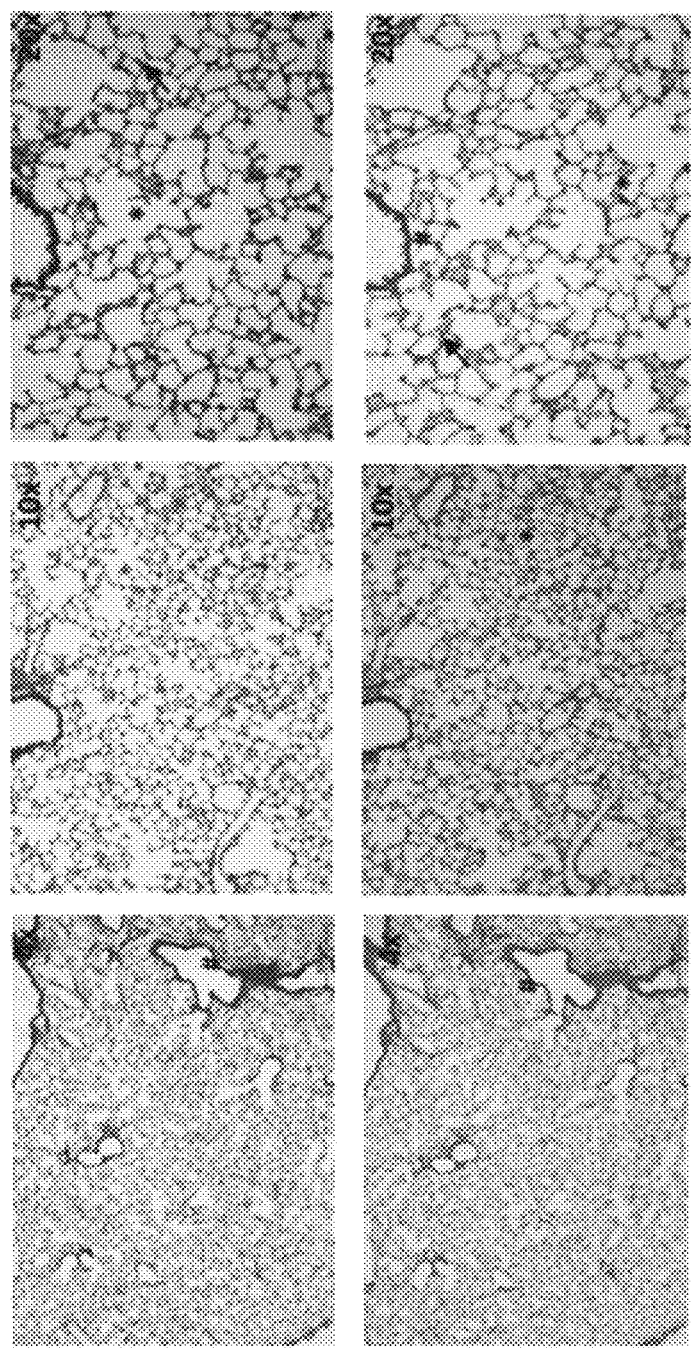
FIGS. 33 to 38 show the results of H&E and Sirius Red staining of the left lung tissues of experimental animal models. Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk; *, Alveolar space; black arrow, Alveolar septa; #, Bronchiole; white arrow head, area with prominent fibrosis; white arrow, area invaded by inflammatory cells.
Figure 34:
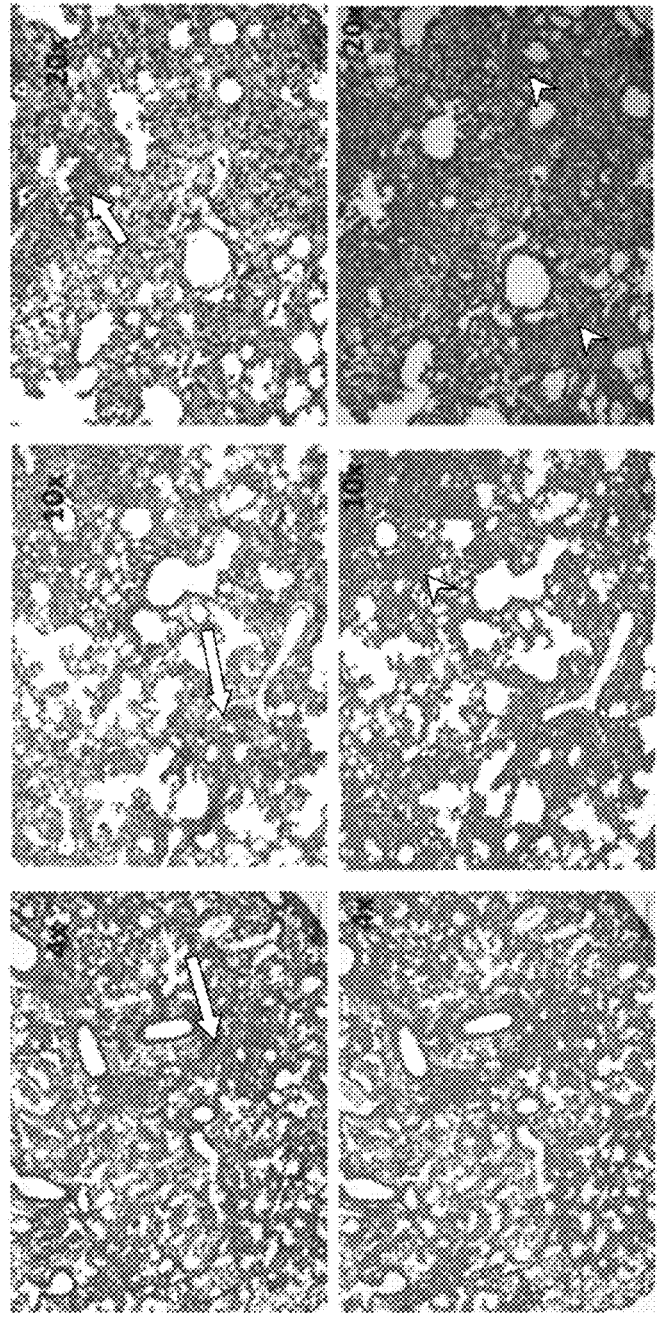
Figure 35:
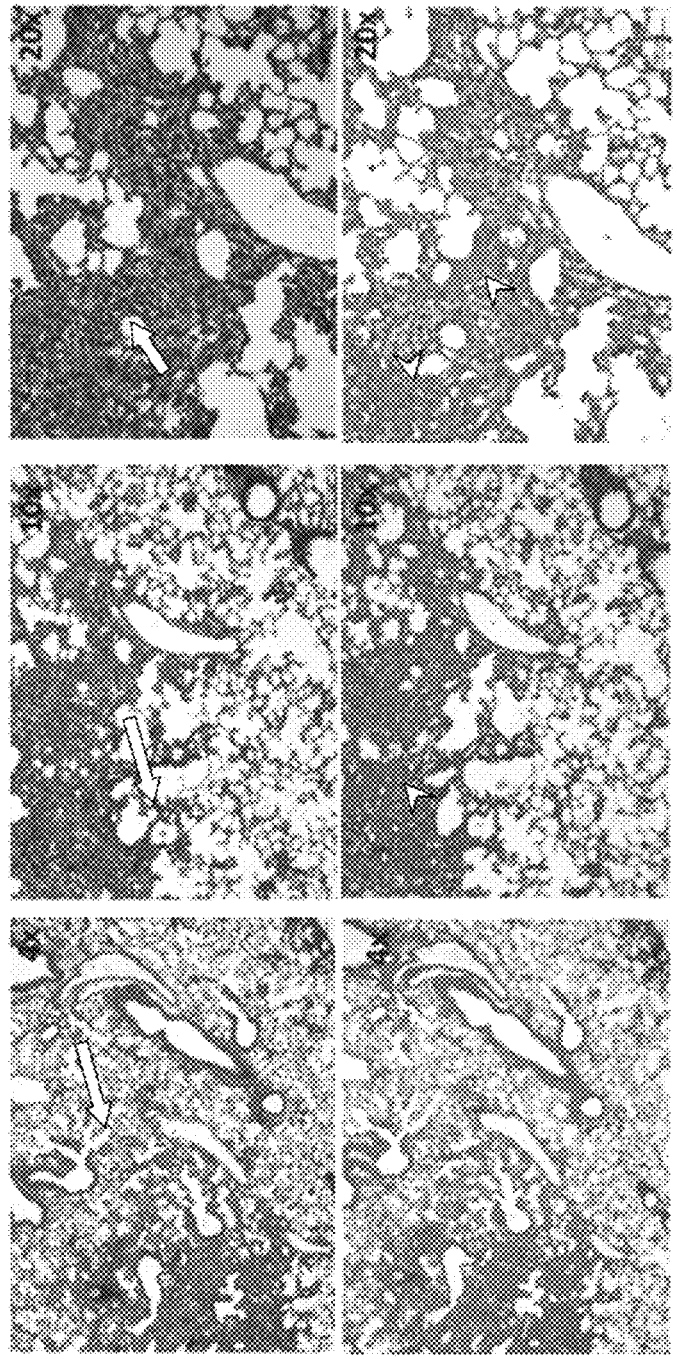
Figure 36:
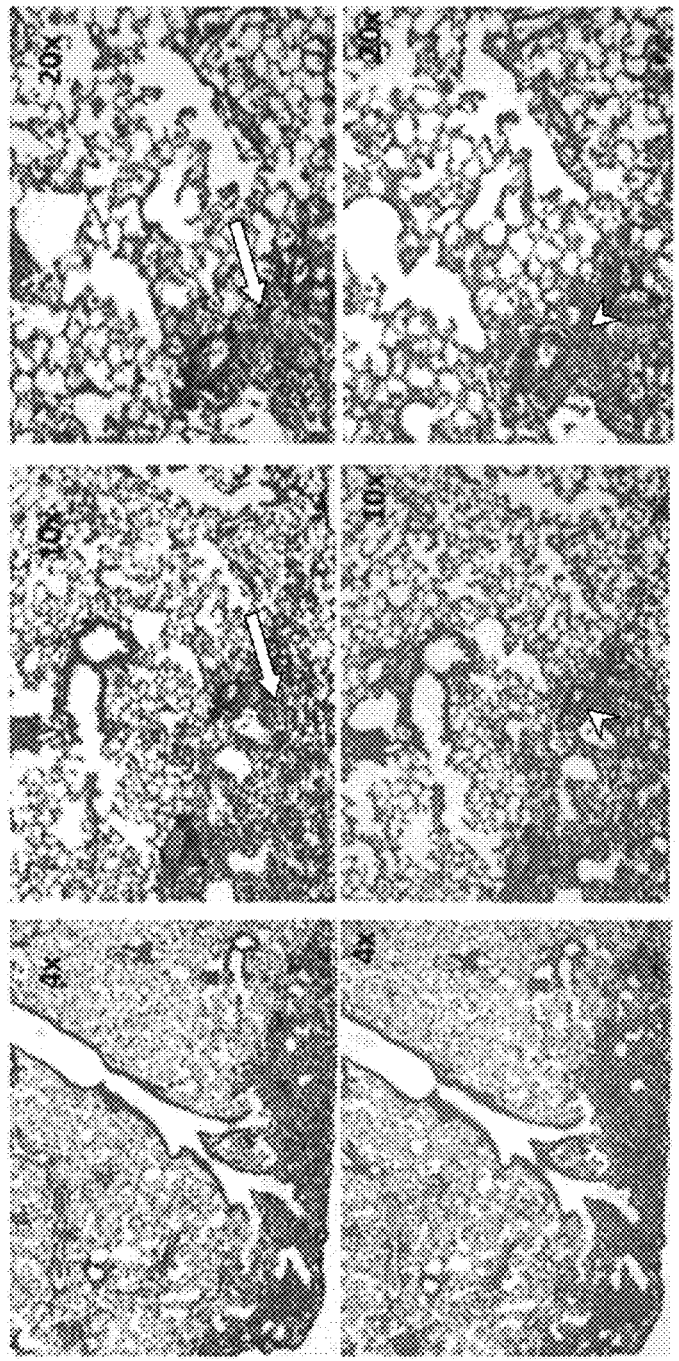
Figure 37:
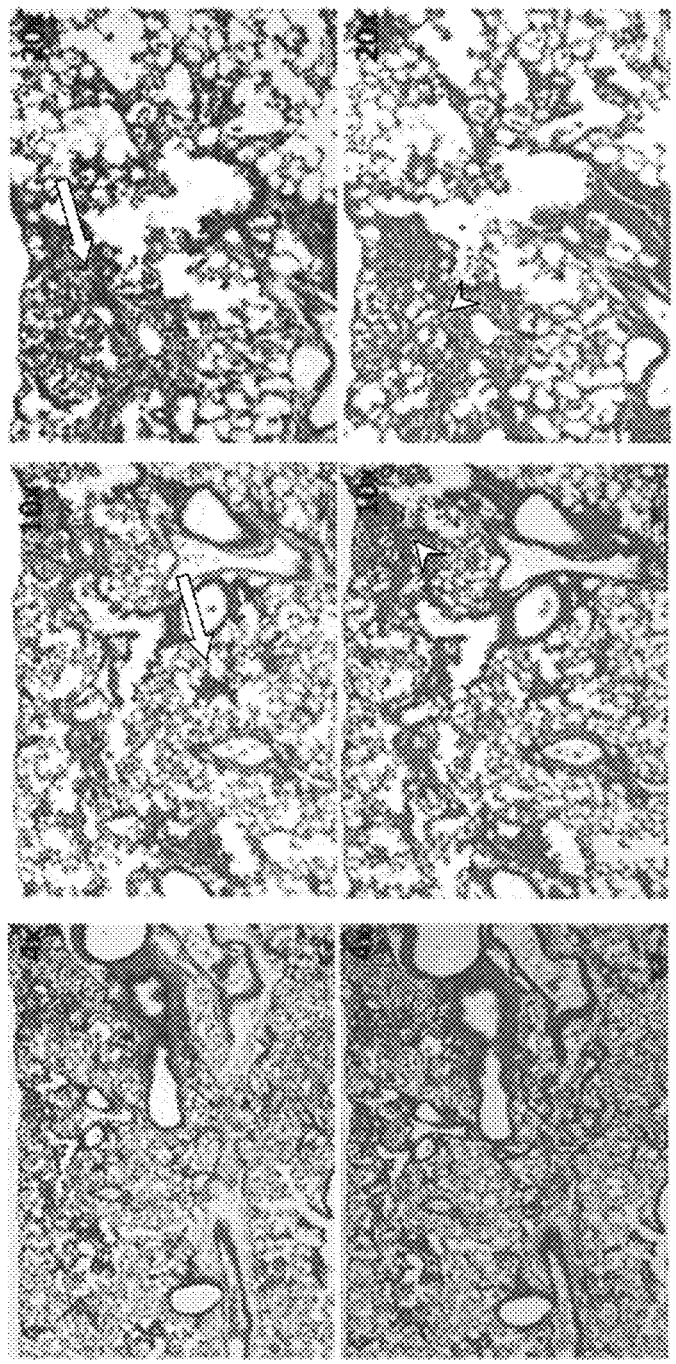
Figure 38:
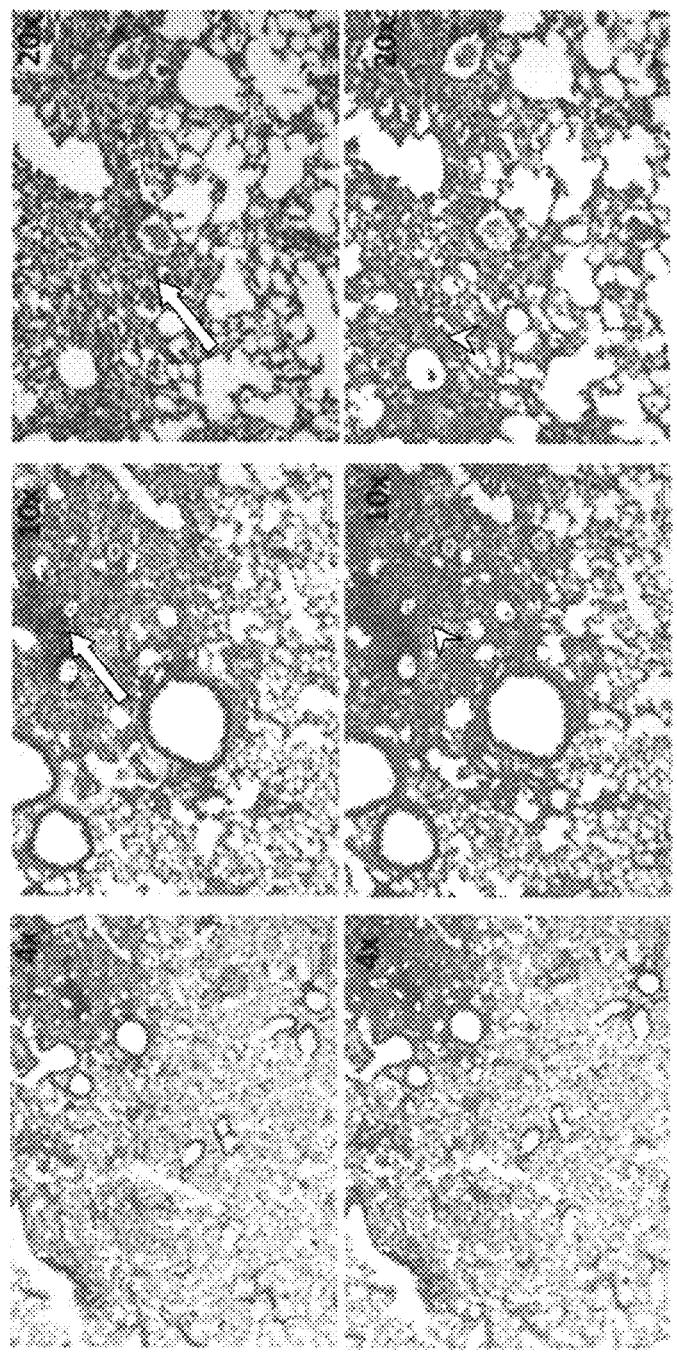

The amounts of the compound present in the plasma and lung of each of the sacrificed mice (finally administered with each compound at 1 hour before sacrifice) were measured. As a result, it was shown that in the group administered with pirfenidone, the concentration of the compound in the plasma and lung was high, whereas in the group administered with the compound of the present invention, the concentration of the compound was relatively very low (see FIGS. 31 and 32). This suggests that although the compound of the present invention was present in the plasma and lung at very lower concentrations than pirfenidone, it exhibited the excellent fibrosis inhibitory effect as described above, supporting the superiority of the compound of the present invention. If it is attempted to formulate the compound of the present invention in various manners, it is expected that the compound of the present invention can effectively treat fibrosis even at lower concentrations.

The pathological conditions of the left lung tissue dissected using a known method were examined by H&E and Sirius Red staining. As a result, it was shown that as pulmonary fibrosis was induced by administration of bleomycin, the densities of cells and proteins in the lung tissue increased, and tissue fibrosis and inflammatory cell invasion were observed, but the compound of the present invention significantly inhibited such fibrosis symptoms (see FIGS. 33 to 38). In particular, it is noted that the inhibitory effect of the compound in the group administered at 10 mpk was the highest compared to that in the groups administered at other concentrations.

Figure 39:
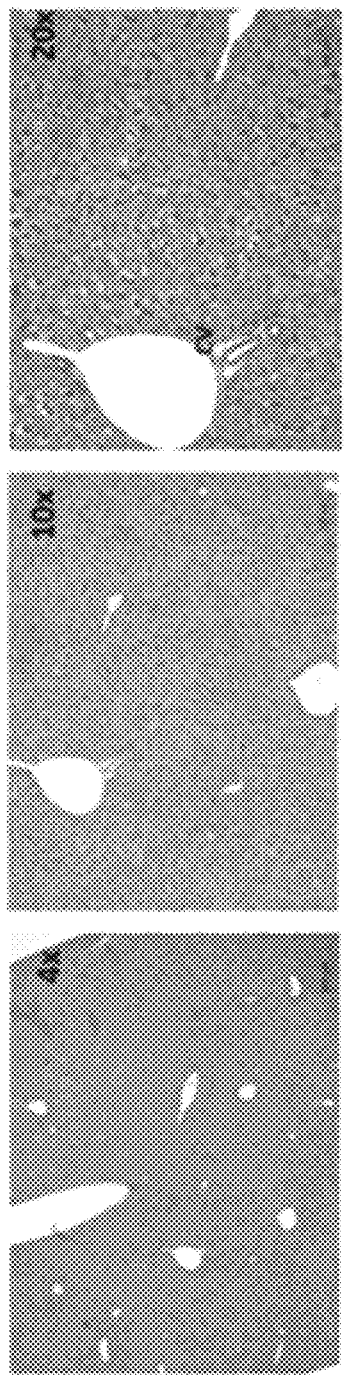
FIGS. 39 to 41 shows the results of H&E staining of the liver tissues of experimental animal models. Sham, a normal animal model; Vehicle Control, a non-compound-treated fibrotic animal model orally administered only with 30% HPCD (hydroxypropyl-beta-cyclodextrin); Pirfenidone 100 mpk PO (30% HPCD), a fibrotic animal model orally administered with Pirfenidone, dissolved in 30% HPCD, at 100 mpk; Compound 1 10-100 mpk PO, fibrotic animal models orally administered with a compound of the present invention, dissolved in 30% HPCD, at 10-100 mpk; CV, Central vein; black arrow, area of necrosis developed.
Figure 39:
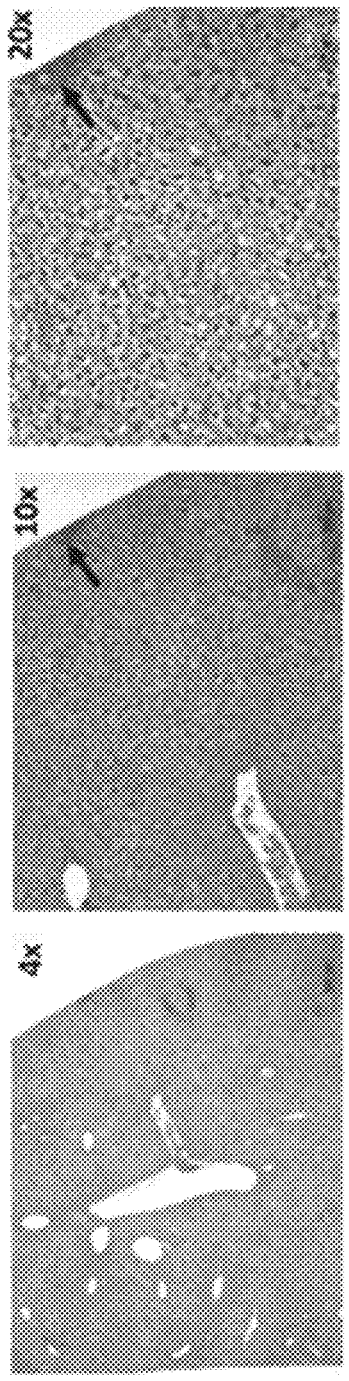
Figure 40:
Figure 40:
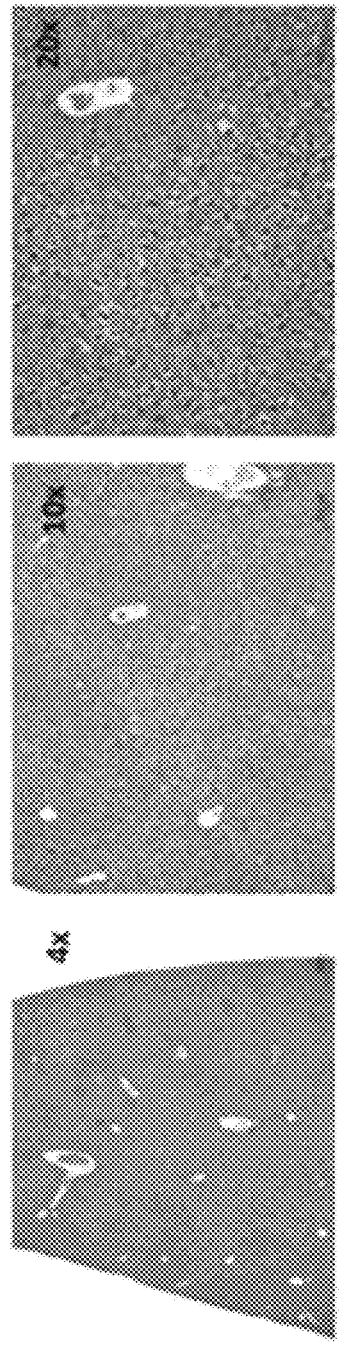
Figure 41:
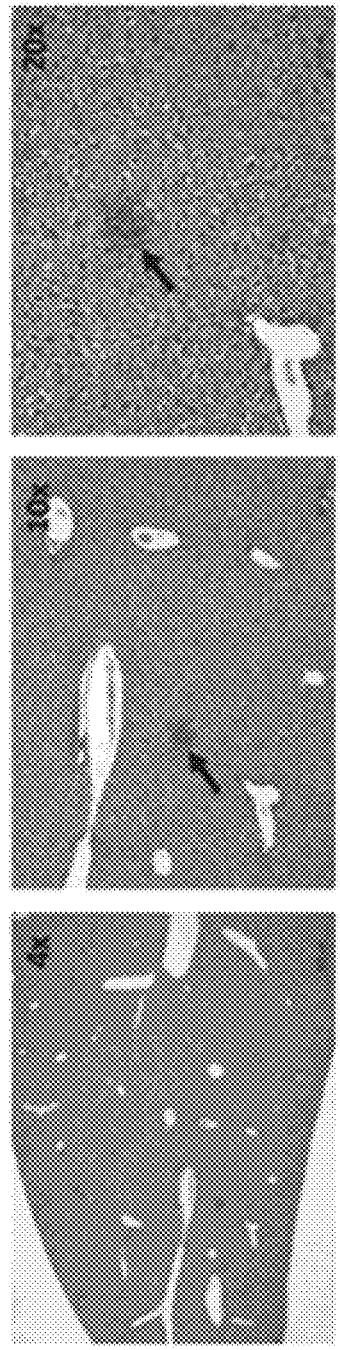
Figure 41:
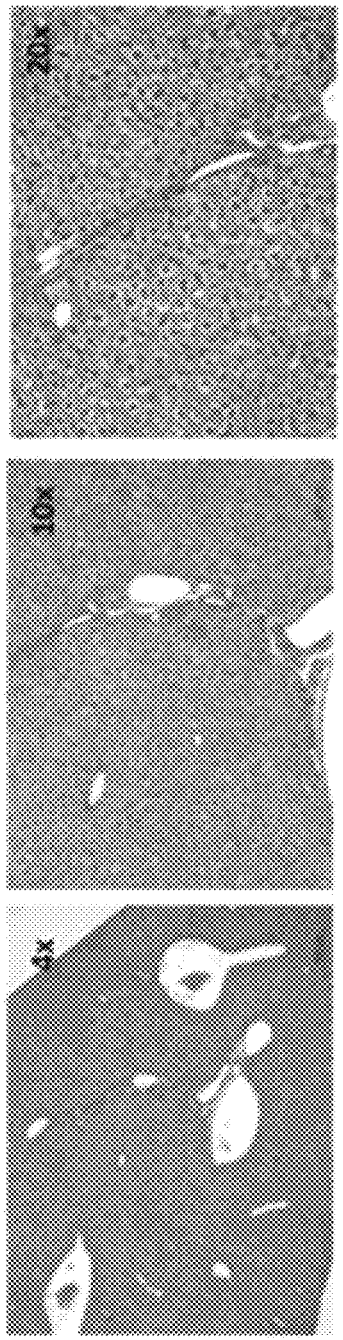

In order to examine the effect of each treatment in this Experiment on the liver, the liver of each of the sacrificed mice was dissected, and the pathological conditions of the liver tissue were examined by H&E staining. As a result, it shown that hepatotoxic symptoms such as liver tissue invasion appeared due to administration of bleomycin, and the group administered with pirfenidone and the groups administered with the compound of the present invention at 50 and 100 mpk also showed hepatotoxic symptoms due to bleomycin, but the group administered with the compound of the present invention at 10 mpk showed the same condition as that of normal liver tissue, even though it was treated with bleomycin (see FIGS. 39 to 41). This suggests that when the compound of the present invention is administered at 10 mpk, it can exhibit a preventive, alleviating or therapeutic effect against hepatotoxicity.

tered with streptozotocin immediately after birth, and fed with high-fat-diet after 3 weeks. Then, in the mouse model, non-alcoholic steatohepatitis occurred at 6 to 9 weeks, and liver fibrosis, cirrhosis and liver cancer occurred within 9 to 12 weeks.

Over 6 to 9 weeks after administration of streptozotocin, the compound of the present invention, dissolved in a mixture solution of Tween80 and 0.5% CMC aqueous solution (1:99 (v/v)) (Formulation Example 2), was orally administered to the animal models once a day (five times a week). As controls, telmisartan and OCA (obeticholic acid) were administered in the same manner.

Figure 42:
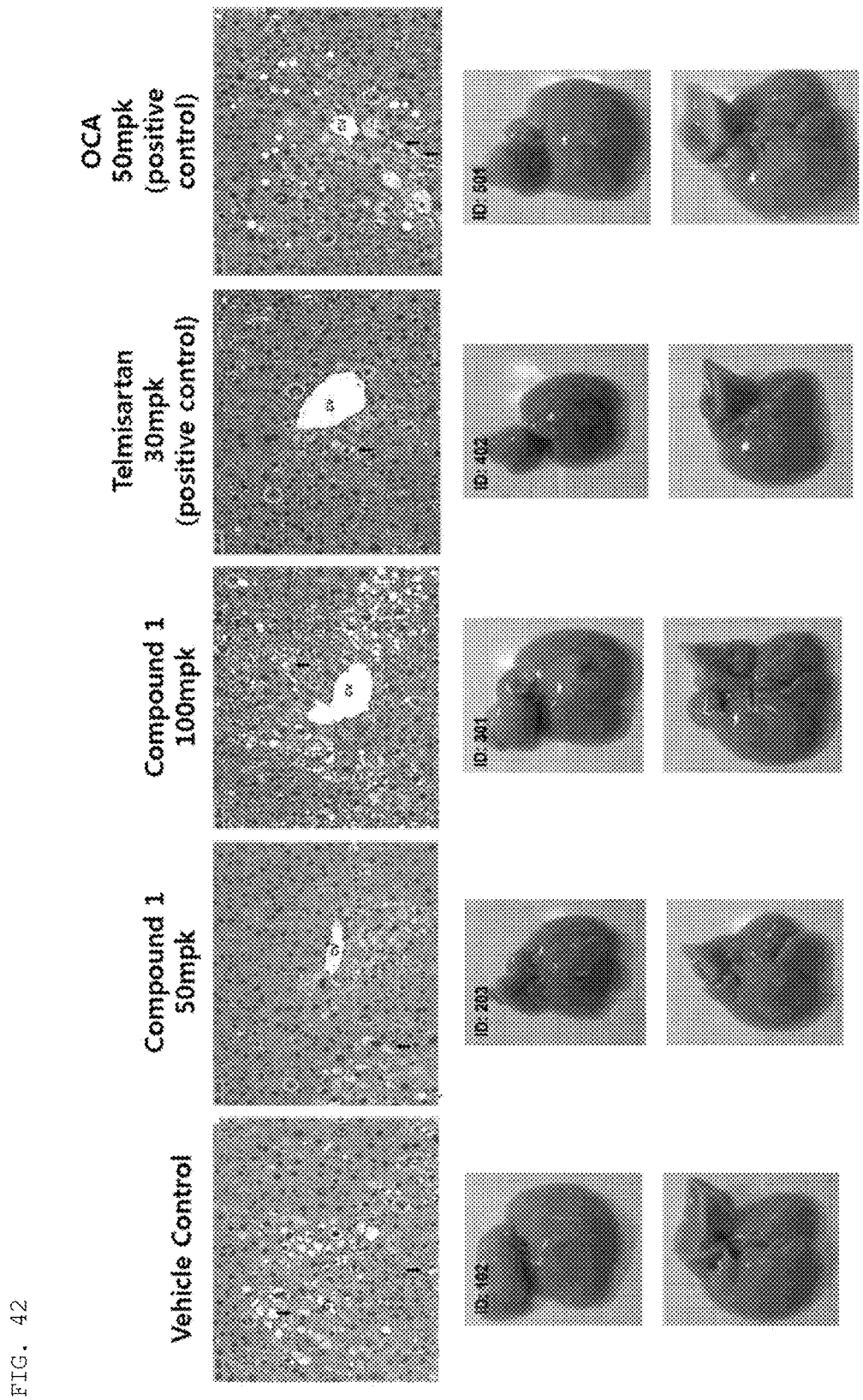
FIG. 42 shows the results of H&E staining of the liver tissues of non-alcoholic steatohepatitis animal models administered with a compound of the present invention or a control compound (telmisartan or OCA), and also shows the morphology of the livers. Vehicle Control, a non-compound-treated non-alcoholic steatohepatitis animal model orally administered only with 0.5% CMC+1% Tween80 aqueous solution; Compound 1 50-100 mpk, a non-alcoholic steatohepatitis animal model orally administered with a compound of the present invention, dissolved in 0.5% CMC+1% Tween80 aqueous solution, at 50-100 mpk; Telmisartan 30 mpk, a non-alcoholic steatohepatitis animal model orally administered with Telmisartan, dissolved in 0.5% CMC+1% Tween80 aqueous solution, at 30 mpk; OCA 50 mpk, a non-alcoholic steatohepatitis animal model orally administered with OCA, dissolved in 0.5% CMC+1% Tween80 aqueous solution, at 30 mpk.
Figure 43:
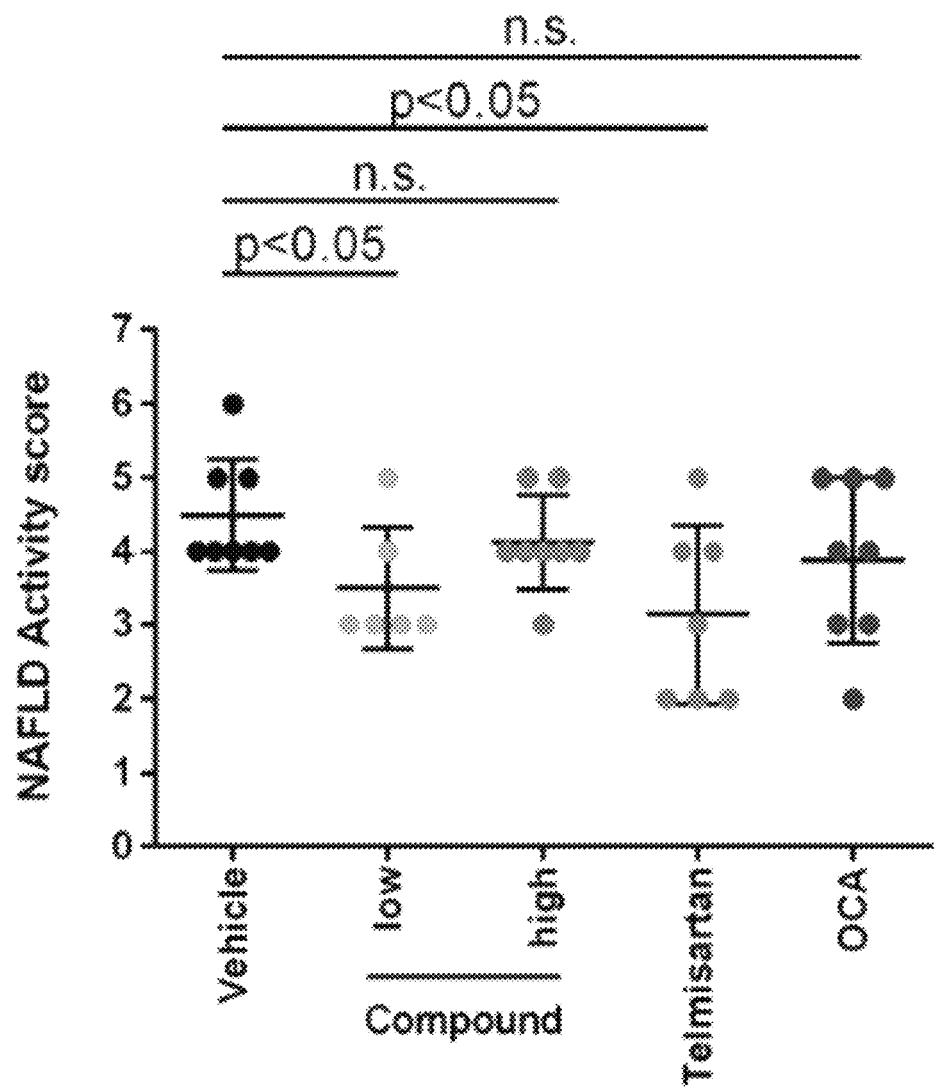
FIG. 43 shows the results of statistically processing the NAFLD (nonalcoholic fatty liver disease) activity score by t-test on the basis of the degrees of inflammation, fibrosis, liver cell ballooning and adipose accumulation in the liver tissues of non-alcoholic steatohepatitis animal models administered with a compound of the present invention or a control compound (telmisartan or OCA). Vehicle Control, a non-compound-treated non-alcoholic steatohepatitis animal model orally administered only with 0.5% CMC+1% Tween80 aqueous solution; Compound low-high, non-alcoholic steatohepatitis animal models orally administered with a compound of the present invention, dissolved in 0.5% CMC+1% Tween80 aqueous solution, at 5-100 mpk; Telmisartan, a non-alcoholic steatohepatitis animal models orally administered with Telmisartan, dissolved in 0.5% CMC+1% Tween80 aqueous solution, at 30 mpk; OCA, a non-alcoholic steatohepatitis animal models orally administered with OCA, dissolved in 0.5% CMC+1% Tween80 aqueous solution, at 30 mpk.

At 8 weeks after administration of streptozotocin (a time point after 3-week administration of the compound), the mice were sacrificed, the liver of each mouse was dissected, the invasion of inflammatory cells was observed by Sirius Red staining of the liver tissue, and fibrosis of the liver tissue was observed by Sirius Red staining (see FIG. 42). In addition, the degrees of inflammation, fibrosis, liver cell ballooning and adipose accumulation observed were measured, data integration was performed, and the NAFLD (nonalcoholic fatty liver disease) activity score was statistically processed by t-test. As a result, it was shown that statistically significant anti-NASH effects appeared in the group administered with the compound of the present invention at 50 mpk and in the group administered with telmisartan at 30 mpk (see FIG. 43).

As described above, the novel compound of the present invention can regulate the activation of EMT (epithelial-mesenchymal transition) by effectively regulating the expression of snail and vimentin which are regulators of EMT, and thus can effectively prevent, alleviate or treat fibrosis. Furthermore, the novel compound of the present invention has very good pharmacokinetics so that it can be absorbed rapidly in vivo even after oral administration, can exhibit stable effects in vivo and can be safely used without significant side effects. In addition, the novel compound of the present invention can effectively inhibit fibrosis of liver cells, and thus can also effectively alleviate or treat non-alcoholic steatohepatitis.

What is claimed is:

1. A compound represented by the Formula 1:

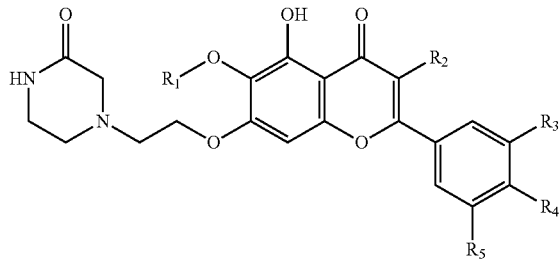

Formula 1 or a pharmaceutically acceptable salt thereof,
wherein:

$R_1$ is $C_{1-5}$ alkyl, $C_{5-6}$ cycloalkyl, $C_{5-6}$ heterocycloalkyl, $C_{6-12}$ aryl or $C_{5-6}$ heteroaryl, where the $C_{5-6}$ heterocycloalkyl and $C_{5-6}$ heteroaryl each independently contain at least one heteroatom selected from the group consisting of oxygen and nitrogen;

$R_2$ is hydrogen, ethyl, acetyl, acetoxy, carboxy, benzoyloxy or 3,4,5-trihydroxybenzoyloxy;

$R_3$ is hydrogen, hydroxy, methyl, methoxy, acetoxy, carboxy or benzyloxy;

$R_4$ is hydrogen, hydroxy, methyl, methoxy, acetoxy, carboxy or benzyloxy; and $R_5$ is hydrogen, hydroxy, methyl, methoxy, acetoxy, carboxy or benzyloxy.

2. The compound according to claim 1, or a pharmaceutically acceptable salt thereof, wherein $R_1$ is methyl, ethyl, cyclopentyl, cyclohexyl or phenyl.

3. The compound according to claim 1, or a pharmaceutically acceptable salt thereof, wherein:

$R_1$ is methyl;

$R_2$ is hydrogen;

$R_3$ is hydrogen, hydroxy or methoxy;

$R_4$ is hydroxy or methoxy; and $R_5$ is hydrogen, hydroxy or methoxy.

4. The compound according to claim 1, wherein the compound is selected from the group consisting of Formula 2, Formula 3, Formula 4 and Formula 5:

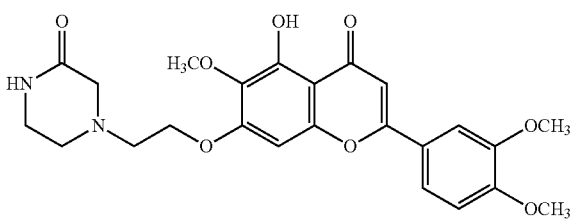

Formula 2

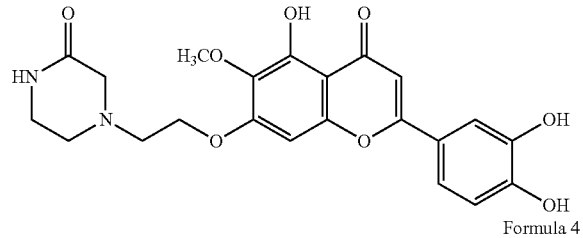

Formula 3

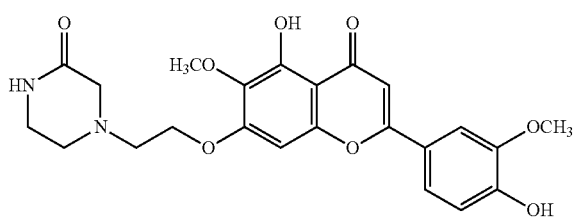

Formula 4 and

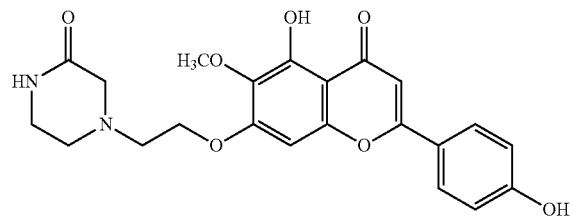

Formula 5 or a pharmaceutically acceptable salt thereof.

5. A pharmaceutical composition comprising a pharmaceutically acceptable carrier and a compound according to claim 1, or a pharmaceutically acceptable salt thereof, as an active ingredient.

6. A comestible composition comprising a comestibly acceptable carrier and a compound according to claim 1, or a comestibly acceptable salt thereof, as an active ingredient.

7. A method for the treatment of fibrosis in a subject, comprising administering to the subject in need thereof a therapeutically effective amount of the pharmaceutical composition according to claim 5.

8. The method of claim 7, wherein the fibrosis is selected from the group consisting of myelofibrosis, liver fibrosis, kidney fibrosis and idiopathic pulmonary fibrosis.

9. A method for the treatment of fibrosis in a subject, comprising administering to the subject in need thereof a therapeutically effective amount of the comestible composition according to claim 6.

10. The method of claim 9, wherein the fibrosis is selected from the group consisting of myelofibrosis, liver fibrosis, kidney fibrosis and idiopathic pulmonary fibrosis.

11. A method for the treatment of non-alcoholic steatohepatitis in a subject, comprising administering to the subject in need thereof a therapeutically effective amount of the pharmaceutical composition according to claim 5.

12. A method for the treatment of non-alcoholic steatohepatitis in a subject, comprising administering to the subject in need thereof a therapeutically effective amount of the comestible composition according to claim 6.

* * * * *